(12) United States Patent
Hirose

(10) Patent No.: US 11,510,751 B2
(45) Date of Patent: Nov. 29, 2022

(54) MEDICAL OBSERVATION APPARATUS

(71) Applicant: Sony Olympus Medical Solutions Inc., Tokyo (JP)

(72) Inventor: Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 134 days.

(21) Appl. No.: 16/970,951

(22) PCT Filed: Jan. 30, 2019

(86) PCT No.: PCT/JP2019/003206
§ 371 (c)(1),
(2) Date: Aug. 19, 2020

(87) PCT Pub. No.: WO2019/167528
PCT Pub. Date: Sep. 6, 2019

(65) Prior Publication Data
US 2020/0390514 A1    Dec. 17, 2020

(30) Foreign Application Priority Data
Feb. 27, 2018 (JP) .............................. JP2018-032865

(51) Int. Cl.
*A61B 90/00*    (2016.01)
*A61B 90/25*    (2016.01)
(Continued)

(52) U.S. Cl.
CPC ............ *A61B 90/361* (2016.02); *A61B 90/25* (2016.02); *G03B 17/561* (2013.01);
(Continued)

(58) Field of Classification Search
CPC ............................ A61B 90/361; G03B 17/561
See application file for complete search history.

(56) References Cited

U.S. PATENT DOCUMENTS

2020/0229894 A1*   7/2020   Chang .................... A61B 90/50

FOREIGN PATENT DOCUMENTS

EP    2119411 A    11/2009
EP    3175810 A1    6/2017
(Continued)

OTHER PUBLICATIONS

International Search Report and Written Opinion dated Apr. 23, 2019 for PCT/JP2019/003206 filed on Jan. 30, 2019, 7 pages including English Translation of the International Search Report.

*Primary Examiner* — Minh Q Phan
(74) *Attorney, Agent, or Firm* — Xsensus LLP

(57) ABSTRACT

A medical observation apparatus including: an arm including a plurality of links connected to each other via a joint, the arm having at least three or more degrees of freedom implemented by a rotation operation about a rotation axis; an imaging device supported by the arm; and an arm controller that controls an operation of the arm. When a posture of the arm is in a predetermined state, and when a predetermined input for moving the arm about a rotation axis orthogonal to a second axis that is a second rotation axis from a side of the arm on which the imaging device is supported and a third axis that is a third rotation axis from the side of the arm on which the imaging device is supported is detected, the arm controller makes one of the links corresponding to the third axis rotate about the third axis.

13 Claims, 10 Drawing Sheets

(51) Int. Cl.
*G03B 17/56* (2021.01)
*H04N 5/225* (2006.01)
*H04N 5/232* (2006.01)
*H01L 27/11519* (2017.01)
*H01L 27/11524* (2017.01)
*H01L 27/11551* (2017.01)
*H01L 27/11565* (2017.01)
*H01L 27/1157* (2017.01)
*H01L 27/11578* (2017.01)
*A61B 90/50* (2016.01)

(52) U.S. Cl.
CPC .... *H01L 27/1157* (2013.01); *H01L 27/11519* (2013.01); *H01L 27/11524* (2013.01); *H01L 27/11551* (2013.01); *H01L 27/11565* (2013.01); *H01L 27/11578* (2013.01); *H04N 5/2253* (2013.01); *H04N 5/23299* (2018.08); *A61B 2090/506* (2016.02)

(56) References Cited

FOREIGN PATENT DOCUMENTS

| | | |
|---|---|---|
| JP | 06-226667 A | 8/1994 |
| JP | 2011-206312 A | 10/2011 |
| JP | 2016-179168 A | 10/2016 |
| WO | WO-2016152046 A1 | 9/2016 |

* cited by examiner

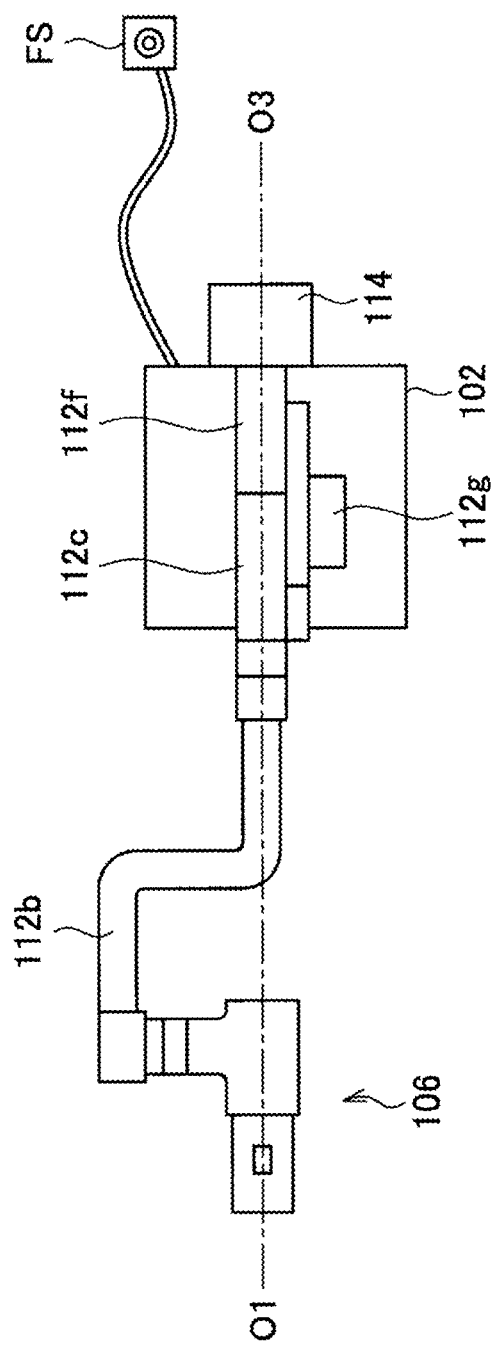

MEDICAL OBSERVATION APPARATUS

CROSS-REFERENCE TO RELATED APPLICATIONS

The present application is based on PCT filing PCT/JP2019/003206, filed Jan. 30, 2019, which claims priority to JP 2018-032865, filed Feb. 27, 2018, the entire contents of each are incorporated herein by reference.

TECHNICAL FIELD

The present disclosure relates to a medical observation apparatus.

BACKGROUND ART

In recent years, medical observation apparatuses have been used in medical practice. This apparatus enables an observation target such as an affected part to be observed with an enlarged view, and thus is used for supporting microsurgery, such as neurosurgery, and for performing endoscopic surgery. Examples of the medical observation apparatus include: a medical observation apparatus including an optical microscope; and a medical observation apparatus including an imaging device that functions as an electronic imaging type microscope. The medical observation apparatus including the optical microscope will be hereinafter referred to as an "optical medical observation apparatus". Furthermore, the medical observation apparatus including the imaging device may be hereinafter referred to as an "electronic imaging type medical observation apparatus" or simply as a "medical observation apparatus". A captured image (moving image or still image) of the observation target captured by the imaging device included in the medical observation apparatus is referred to as a "medical captured image".

The electronic imaging type medical observation apparatus can achieve image quality equal to or higher than that of an optical medical observation apparatus, due to, for example, improvement of the image quality of the imaging device and of a display device for displaying the captured image. In the electronic imaging type medical observation apparatus, the imaging device is supported by, for example, an arm having predetermined degrees of freedom, rendering the position of the imaging device movable. The electronic imaging type medical observation apparatus does not require it's user (for example, a medical worker such as an operator or an assistant of the operator, who may be hereinafter simply referred to as a "user") to look into an eyepiece of an optical microscope as in the case where the optical medical observation apparatus is used, whereby the position of the imaging device can be more freely moved. Thus, the use of the electronic imaging type medical observation apparatus offers such an advantage that the operation can be supported more flexibly with the movement of the position of the imaging device. As a result, popularity of the electronic imaging type medical observation apparatuses in the medical practice has been increasing.

Meanwhile, techniques related to control of a multi-axis manipulator have been under development. For example, Patent Literature 1 below discloses a technique related to control of a seven-axis manipulator.

CITATION LIST

Patent Literature

Patent Literature 1: JP H6-226667 A

DISCLOSURE OF INVENTION

Technical Problem

As described above, since the user of the electronic imaging type medical observation apparatus can freely move the position of the imaging device. This means that the user can change the imaging range by moving the position of the imaging device. However, the degrees of freedom of the arm, which supports the imaging device, are compromised depending on its posture. Thus, there may be "cases where the imaging device cannot be moved to capture an image within a desired imaging range unless the user manually changes the posture of the arm". When such a case occurs, the usability for the user of the medical observation apparatus may be compromised.

The present disclosure proposes a new and improved medical observation apparatus capable offering higher usability to its users.

Solution to Problem

According to the present disclosure, there is provided a medical observation apparatus including: an arm including a plurality of links connected to each other via a joint, the arm having at least three or more degrees of freedom implemented by a rotation operation about a rotation axis; an imaging device supported by the arm; and an arm controller configured to control an operation of the arm, wherein when a posture of the arm is in a predetermined state, and when a predetermined input for moving the arm about a rotation axis orthogonal to a second axis that is a second rotation axis from a side of the arm on which the imaging device is supported and a third axis that is a third rotation axis from the side of the arm on which the imaging device is supported is detected, the arm controller rotates one of the links corresponding to the third axis about the third axis.

Advantageous Effects of Invention

According to the present disclosure, the usability for a user using a medical observation apparatus can be improved.

Note that the above effect is not necessarily limiting, and any other effects that are described in the present specification or that can be grasped from the present specification may be achieved in addition to or in place of the above effect.

BRIEF DESCRIPTION OF DRAWINGS

FIG. 11 is an explanatory diagram illustrating an example of the configuration of the medical observation apparatus according to the present embodiment.

BEST MODE FOR CARRYING OUT THE INVENTION

Figure 1:
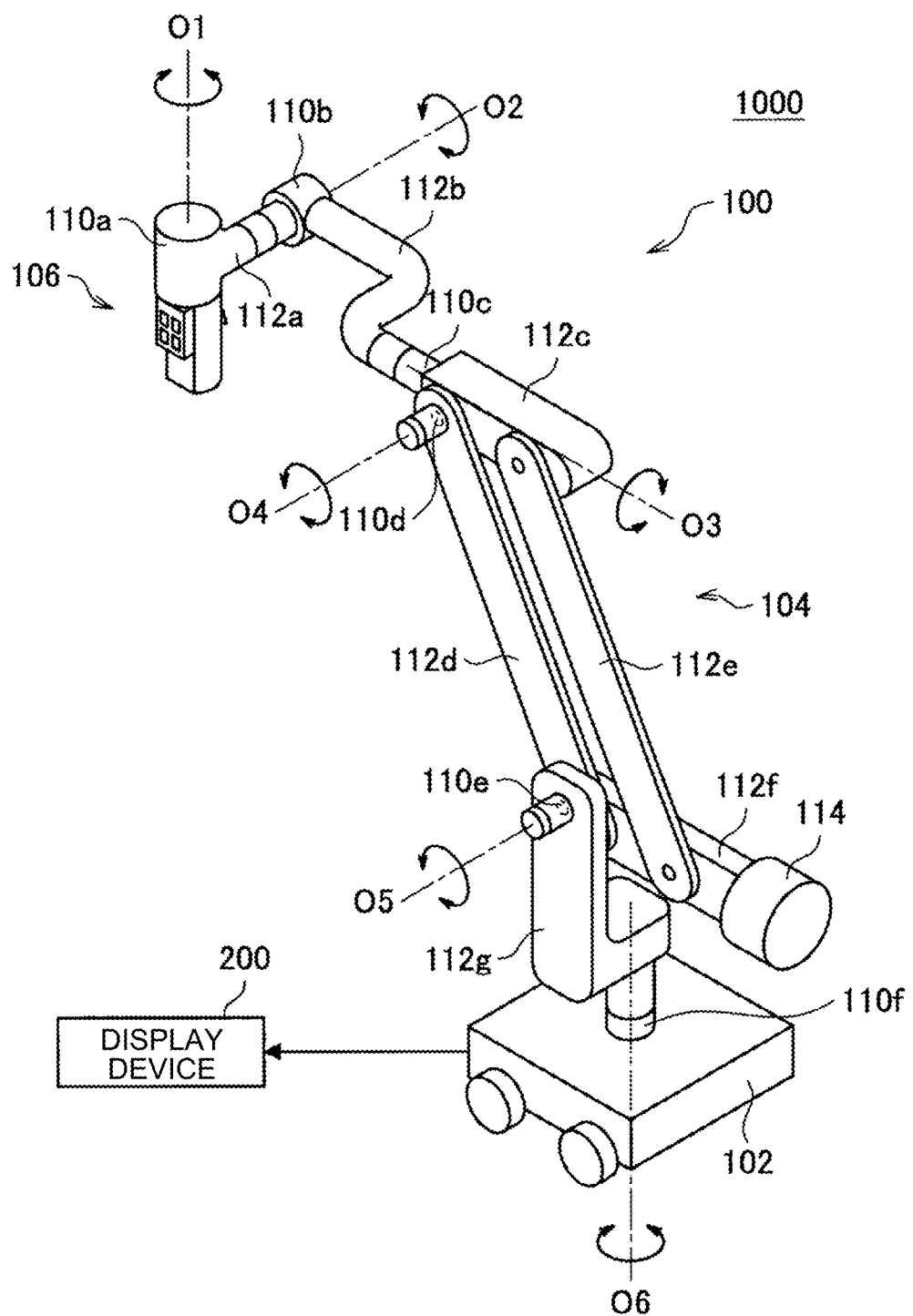
FIG. 1 is an explanatory diagram illustrating an example of the configuration of a medical observation system according to the present embodiment.

Hereinafter, preferred embodiments of the present disclosure will be described in detail with reference to the accompanying drawings. In the specification and the drawings, components having substantially the same function and configuration are denoted by the same reference numerals, and redundant description is omitted.

Hereinafter, description will be made in the following order.

1. Medical observation system according to the present embodiment and control method according to the present embodiment
[1] Configuration of medical observation system
[1-1] Display device 200
[1-2] Medical observation apparatus 100
[2] Control method according to the present embodiment
[2-1] Overview of control method according to the present embodiment
[2-2] Processing in control method according to the present embodiment
[3] Example of effects achieved by using control method according to the present embodiment
2. Program according to the present embodiment (Medical Observation System According to the Present Embodiment and Control Method According to the Present Embodiment)

Hereinafter, a control method according to the present embodiment will be described while describing an example of a medical observation system according to the present embodiment.

A case where the medical observation apparatus according to the present embodiment executes processing in the control method according to the present embodiment will be described below. Specifically, a case where the medical observation apparatus according to the present embodiment functions as a medical control apparatus will be described.

It should be noted that in the medical observation system according to the present embodiment, an apparatus that functions as the medical control apparatus is not limited to the medical observation apparatus according to the present embodiment. For example, in the medical observation system according to the present embodiment, any apparatus such as a medical controller capable of executing the processing in the control method according to the present embodiment may function as the medical control apparatus.

[1] Configuration of Medical Observation System

FIG. 1 is a diagram illustrating the configuration of a medical observation system 1000 according to the present embodiment. The medical observation system 1000 includes, for example, a medical observation apparatus 100 and a display device 200.

Note that the medical observation system according to the present embodiment is not limited to the example illustrated in FIG. 1.

For example, the medical observation system according to the present embodiment may further include a medical control apparatus (not illustrated) that controls various operations in the medical observation apparatus 100. FIG. 1 illustrates an example where, in the medical observation system 1000, as described below, the medical observation apparatus 100 includes a control unit (described later) that executes processing in the control method according to the present embodiment, and thus has a function of the medical control apparatus (not illustrated).

Examples of the medical control apparatus (not illustrated) include any device that can execute the processing in the control method according to the present embodiment, such as a "medical controller" or a "computer such as a server". Furthermore, the medical control apparatus (not illustrated) may be, for example, an integrated circuit (IC) that can be embedded in the above-described device.

Furthermore, the medical observation system according to the present embodiment may have a configuration including a plurality of the medical observation apparatuses 100 and the display devices 200. When a plurality of the medical observation apparatuses 100 is provided, each of the medical observation apparatuses 100 executes the processing in the control method of the medical observation apparatus 100 described later. Furthermore, when the medical observation system according to the present embodiment has a configuration including a plurality of the medical observation apparatuses 100 and the display devices 200, the medical observation apparatuses 100 and the display devices 200 may be associated with each other in one-to-one relationship, or a plurality of medical observation apparatuses 100 may be associated with a single display device 200. When a plurality of medical observation apparatuses 100 is associated with a single display device 200, the display device 200 performs a switching operation or the like, for example, so that the medical observation apparatus 100 a medical captured image captured by which is displayed on the display screen is switched.

Figure 2:
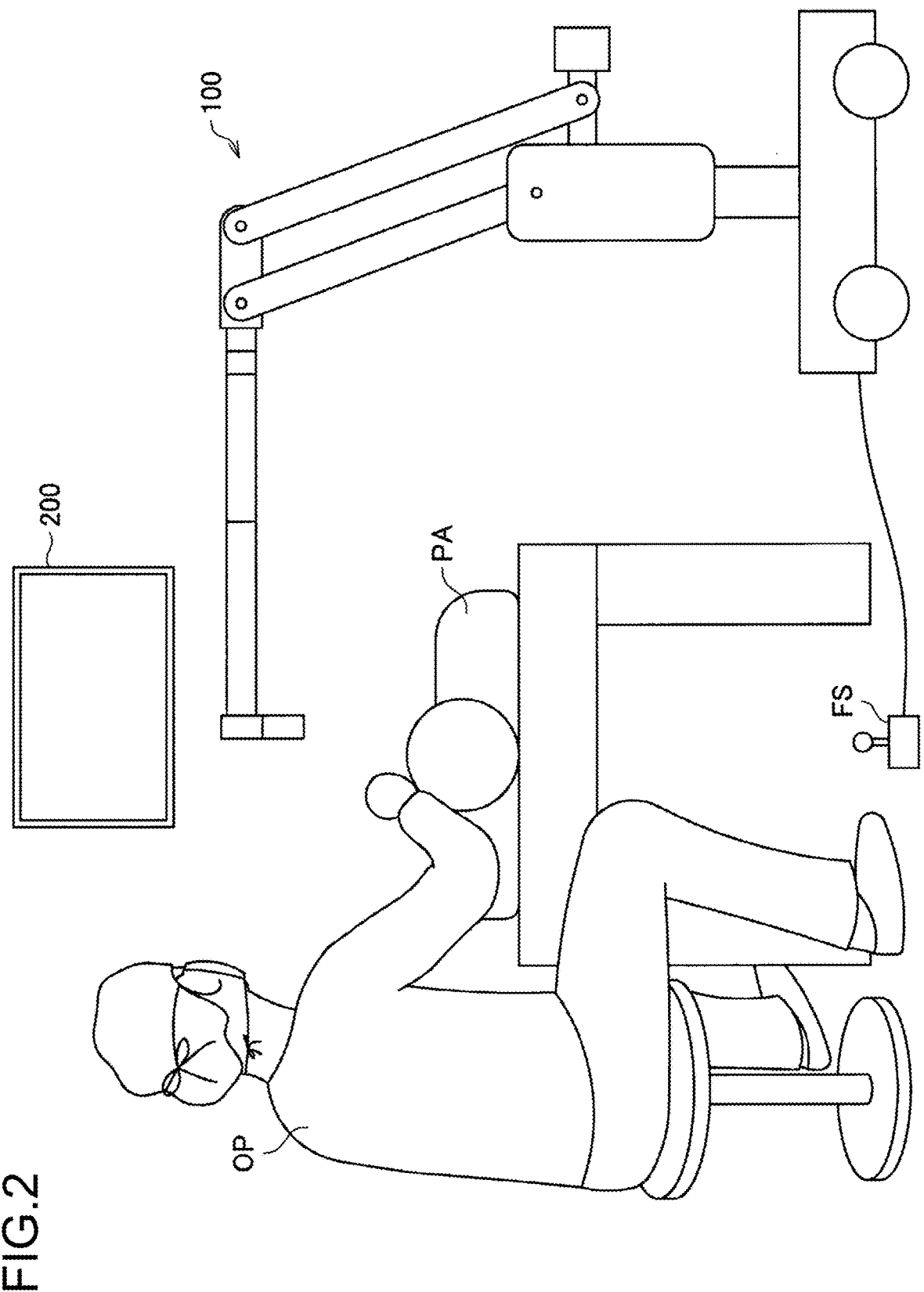
FIG. 2 is an explanatory diagram illustrating an example of a use case in which the medical observation system according to the present embodiment is used.

FIG. 2 is an explanatory diagram illustrating an example of a use case in which the medical observation system 1000 according to the present embodiment is used.

An imaging device (to be described later) included in the medical observation apparatus 100 captures an image of a patient PA as an observation target (a patient who receives medical treatment). The captured image obtained by capturing an image of the patient who receives medical treatment is an example of the medical captured image.

The medical captured image captured by the medical observation apparatus 100 is displayed on the display screen of the display device 200. Then, an operator OP who performs medical treatment using the medical observation apparatus 100 (An example of the user of the medical observation apparatus 100. The same applies in the following description) performs the medical treatment on the patient PA while watching the medical captured image displayed on the display screen of the display device 200.

Furthermore, the operator OP achieves a desired state of the medical observation apparatus 100 by operating an operation device (such as a foot switch FS) external to the medical observation apparatus 100 or an operation device (described later) included in the medical observation apparatus 100, and thus operating the an arm (described later) and an imaging device (described later) included in the medical observation apparatus 100.

Hereinafter, each device of the medical observation system 1000 will be described.

[1-1] Display Device 200

The display device 200 is a display unit in the medical observation system 1000, and corresponds to a display device external to the medical observation apparatus 100. For example, the display device 200 displays on the display screen, various images such as a medical captured image (moving image or still image) captured by the medical observation apparatus 100 and an image related to a user interface (UI). Furthermore, the display device 200 may have a configuration capable of performing 3D display through any appropriate system. The displaying by the display device 200 is controlled by, for example, the medical observation apparatus 100 or the medical control apparatus (not illustrated).

In the medical observation system 1000, the display device 200 is installed at any location such as a wall surface, a ceiling, and a floor surface of an operating room that can be visually recognized by a person involved in an operation, such as an operator, in the operating room. Examples of the display device 200 include a liquid crystal display, an organic electro-luminescence (EL) display, a cathode ray tube (CRT) display, and the like.

Note that the display device 200 is not limited to the example described above.

For example, the display device 200 may be any wearable device used by the operator or the like worn on the body, such as a head-mounted display or an eyewear-type device.

The display device 200 is driven by, for example, power supplied from an internal power supply such as a battery included in the display device 200 or power supplied from a connected external power supply.

[1-2] Medical Observation Apparatus 100

The medical observation apparatus 100 is an electronic imaging type medical observation apparatus. For example, when the medical observation apparatus 100 is used during surgery, the operator (an example of a user of the medical observation apparatus 100) performs various treatments such as procedures in accordance with the surgical procedure on a surgical site (affected part), while observing the surgical site by referring to the medical captured image captured by the medical observation apparatus 100 and displayed on the display screen of the display device 200.

As illustrated in FIG. 1, the medical observation apparatus 100 includes, for example, a base 102, an arm 104, and an imaging device 106.

Although not illustrated in FIG. 1, the medical observation apparatus 100 may include, for example, one or more processors (not illustrated) including an arithmetic circuit such as a micro processing unit (MPU), a read only memory (ROM) (not illustrated), a random access memory (RAM) (not illustrated), a recording medium (not illustrated), and a communication device (not illustrated). The medical observation apparatus 100 is driven by, for example, power supplied from an internal power supply such as a battery included in the medical observation apparatus 100 or power supplied from a connected external power supply.

The processor (not illustrated) functions as a control unit (described later) in the medical observation apparatus 100. The ROM (not illustrated) stores control data such as a program and a calculation parameter used by the processor (not illustrated). The RAM (not illustrated) temporarily stores a program executed by the processor (not illustrated) and the like.

The recording medium (not illustrated) functions as a storage unit (not illustrated) in the medical observation apparatus 100. The recording medium (not illustrated) stores various types of data such as data related to the control method according to the present embodiment as well as various applications, for example. Here, examples of the recording medium (not illustrated) include a magnetic recording medium such as a hard disk, and a nonvolatile memory such as a flash memory. Furthermore, the recording medium (not illustrated) may be removable from the medical observation apparatus 100.

The communication device (not illustrated) is a communication unit included in the medical observation apparatus 100, and is in charge of performing wireless or wired communications with an external device such as the display device 200. Here, for example, as the communication device (not illustrated), an IEEE 802.15.1 port and a transmission/reception circuit (wireless communication), an IEEE 802.11 port and a transmission/reception circuit (wireless communication), a communication antenna and an RF circuit (wireless communication), or a LAN terminal and a transmission/reception circuit (wired communication) may be used.

[1-2-1] Base 102

The base 102 is a base of the medical observation apparatus 100, and has one end of the arm 104 connected thereto, to support the arm 104 and the imaging device 106.

The base 102 is provided with, for example, casters, and the medical observation apparatus 100 is grounded to the floor via the casters. With the casters provided, the medical observation apparatus 100 can easily move on the floor surface by the casters.

[1-2-2] Arm 104

The arm 104 includes a plurality of links connected to each other via joints. The arm 104 has at least three or more degrees of freedom implemented by a rotation operation about rotation axes described later. The three or more degrees of freedom of the arm 104 include degrees of freedom implemented by a rotation operation about a first axis O1, a second axis O2, and a third axis O3 described later. The example illustrated in FIG. 1 is an example of a configuration having six degrees of freedom as described later.

Furthermore, the arm 104 supports the imaging device 106. The imaging device 106 supported by the arm 104 can move three-dimensionally, and the position and posture of the moved imaging device 106 are held by the arm 104.

More specifically, the arm 104 includes, for example, a plurality of joints 110*a*, 110*b*, 110*c*, 110*d*, 110*e*, and 110*f* and a plurality of links 112*a*, 112*b*, 112*c*, 112*d*, 112*e*, 112*f*, and 112*g* connected via the joints 110*a*, 110*b*, 110*c*, 110*d*, 110*e*, and 110*f*. The rotatable range of each of the joints 110*a*, 110*b*, 110*c*, 110*d*, 110*e*, and 110*f* is set as appropriate in a design stage, a manufacturing stage, or the like so that a desired movement of the arm 104 is implemented.

Specifically, in the medical observation apparatus 100 illustrated in FIG. 1, the six rotation axes (the first axis O1, the second axis O2, the third axis O3, the fourth axis O4, the fifth axis O5, and the sixth axis O6) corresponding to the six joints 110*a*, 110*b*, 110*c*, 110*d*, 110*e*, and 110*f* forming the arm 104 are provided, whereby the six degrees of freedom are implemented for the movement of the imaging device 106. More specifically, in the medical observation apparatus 100 illustrated in FIG. 1, a movement with three degrees of freedom for translation and three degrees of freedom for rotation (a total of six degrees of freedom) is implemented.

The first axis O1 is the first rotation axis from the side of the arm 104 where the imaging device 106 is supported. The second axis O2 is the second rotation axis from the side of the arm 104 where the imaging device 106 is supported. The third axis O3 is the third rotation axis from the side of the arm 104 where the imaging device 106 is supported. The fourth axis O4 is the fourth rotation axis from the side of the arm 104 where the imaging device 106 is supported. The fifth axis O5 is the fifth rotation axis from the side of the arm 104 where the imaging device 106 is supported. The sixth axis O6 is the sixth rotation axis from the side of the arm 104 where the imaging device 106 is supported.

For example, each of the joints 110*a*, 110*b*, 110*c*, 110*d*, 110*e*, and 110*f* is provided with an actuator (not illustrated), and rotates about the corresponding one of the rotation axes in response to the driving of the actuator (not illustrated). The driving of the actuator (not illustrated) is controlled by, for example, a processor functioning as a control unit described later, or an external medical control apparatus (not illustrated).

In the medical observation apparatus 100, the actuator (not illustrated) may be provided only to some of the joints 110*a*, 110*b*, 110*c*, 110*d*, 110*e*, and 110*f*. Examples of the configuration in which the actuator (not illustrated) is only provided to some of the joints include "a configuration in which the actuator (not illustrated) is provided to the joints 110*a*, 110*b*, and 110*c* and is not provided to the joints 110*d*, 110*e*, and 110*f*".

For example, each of the joints 110*a*, 110*b*, 110*c*, 110*d*, 110*e*, and 110*f* may be provided with an angle sensor (not illustrated) capable of detecting a rotation angle on each of the six rotation axes. Examples of the angle sensor according to the present embodiment include any sensor that can obtain a rotation angle on each of the six rotation axes, such as a rotary encoder and an angular velocity sensor.

In the medical observation apparatus 100, the angle sensor (not illustrated) may be provided only to some of the joints 110*a*, 110*b*, 110*c*, 110*d*, 110*e*, and 110*f*. Examples of the configuration in which the angle sensor (not illustrated) is only provided to some of the joints include "a configuration in which the angle sensor (not illustrated) is provided to the joints 110*a*, 110*b*, and 110*c* and is not provided to the joints 110*d*, 110*e*, and 110*f*".

Note that the sensor provided to the arm 104 is not limited to the angle sensor. For example, the arm 104 may be provided with a sensor for detecting an external force applied to the arm 104. The sensor for detecting an external force applied to the arm 104 is in charge of detecting a predetermined input (described later) to the arm 104.

An example of the sensor for detecting an external force applied to the arm 104 includes any sensor capable of detecting a force, such as a load cell. The sensor for detecting an external force applied to the arm 104 in the medical observation apparatus 100 can function as, for example, a sensor for detecting the moving direction of the imaging device 106.

The sensor for detecting an external force applied to the arm 104 is disposed, for example, between the joint 110*a* corresponding to the first axis O1 and the joint 110*b* corresponding to the second axis O2, that is, in a link 112*a* portion.

The example of the arrangement of the sensor for detecting an external force applied to the arm 104 is not limited to the example described above. For example, a sensor for detecting an external force applied to the arm 104 may be provided in a link 112*b* portion.

For example, each of the joints 110*a*, 110*b*, 110*c*, 110*d*, 110*e*, and 110*f* is rotated about a corresponding rotation axis by the driving of the actuator (not illustrated), for example, so that various operations of the arm 104 such as extension or contraction (folding) of the arm 104 can be implemented. In addition, the various operations of the arm 104 such as extension or contraction (folding) of the arm 104 for example can be implemented with the joints 110*a*, 110*b*, 110*c*, 110*d*, 110*e*, and 110*f* each rotating about the corresponding rotation axis in response to an operation of the user.

The joint 110*a* has a substantially cylindrical shape, and has a distal end portion (a lower end portion in FIG. 1) supporting the imaging device 106 (the upper end portion of the imaging device 106 in FIG. 1) so that the imaging device 106 can rotate about a rotation axis (first axis O1) parallel to the center axis of the imaging device 106. Here, the medical observation apparatus 100 illustrated in FIG. 1 is configured such that the first axis O1 matches the optical axis of the imaging device 106. In other words, the first axis O1 is coaxial with the optical axis of the imaging device 106. Thus, by rotating the imaging device 106 about the first axis O1 illustrated in FIG. 1, an image whose visual field is changed in a rotating manner is captured as the medical captured image captured by the imaging device 106. Needless to say, the configuration of the medical observation apparatus 100 is not limited to the configuration in which the first axis O1 is coaxial with the optical axis of the imaging device 106.

The link 112*a* is a substantially rod-shaped member by which the joint 110*a* is fixedly supported. The link 112*a* extends, for example, in a direction orthogonal to the first axis O1, and is connected to the joint 110*b*.

The joint 110*b* has a substantially cylindrical shape, and supports the link 112*a* so that the link 112*a* can rotate about a rotation axis (second axis O2) orthogonal to the first axis O1. The link 112*b* is fixedly connected to the joint 110*b*.

The link 112*b* is a substantially L-shaped member whose one side extends in a direction orthogonal to the second axis O2, and is connected to each of the joint 110*b* and the joint 110*c*.

The joint 110*c* has a substantially cylindrical shape, and supports the link 112*b* so that the link 112*b* can rotate at least about a rotation axis (third axis O3) orthogonal to the second axis O2. One end of the link 112*c* is fixedly connected to the joint 110*c*.

Here, with the distal end side of the arm 104 (the side on which the imaging device 106 is provided) rotating about the second axis O2 and the third axis O3, the imaging device 106 can be moved to have the position of the imaging device 106 changed in the horizontal plane. That is, in the medical observation apparatus 100, the rotation about the second axis O2 and the rotation about the third axis O3 are controlled, so that the visual field of the medical captured image can be moved in a plane.

The link 112c is connected to the link 112b via the joint 110c, and is connected to the link 112d via the joint 110d. The link 112c is connected to the link 112e.

The joint 110d supports the link 112c so that the link 112c can rotate about a rotation axis (the fourth axis O4) orthogonal to the third axis O3. The link 112d is connected to the joint 110d.

The link 112d is connected to the link 112c via the joint 110d, and connected to the link 112g via the joint 110e. The link 112d is connected to the link 112f.

The link 112e is connected to each of the link 112c and the link 112f.

The link 112f is connected to each of the link 112d and the link 112e. A counterweight 114 is provided at one end of the link 112f. The counterweight 114 has the mass and the arranged position adjusted so that the mass of components provided more on the distal end side of the arm 104 (the side on which the imaging device 106 is provided) than the counterweight 114 can cancel out the rotation moment produced about the fourth axis O4 and the rotation moment produced about the fifth axis O5.

The joint 110e supports one end of the link 112d so that the link 112d can rotate about a rotation axis (fifth axis O5) parallel to the fourth axis O4. One end of the link 112g is connected to the joint 110e.

Here, the fourth axis O4 and the fifth axis O5 are rotation axes with which the imaging device 106 may be moved in the vertical direction. With the distal end side of the arm 104 (the side on which the imaging device 106 is provided) rotating about the fourth axis O4 and the fifth axis O5, the position of the imaging device 106 in the vertical direction changes. Thus, with the distal end side of the arm 104 (the side on which the imaging device 106 is provided) rotating about the fourth axis O4 and the fifth axis O5, the distance between the imaging device 106 and an observation target such as a patient's surgical site can be changed.

The link 112g is a member as a combination of a first member that has a substantially L shape with one side extending in the vertical direction and the other side extending in the horizontal direction, and a rod-shaped second member extending vertically downward from a portion of the first member extending in the horizontal direction. The joint 110e is fixedly connected to a portion of first member of the link 112g extending in the vertical direction. The joint 110f is connected to the second member of the link 112g.

The link 112f and the base 102 are connected to the joint 110f. The joint 110f supports the link 112g so that the link 112g can rotate about a rotation axis (sixth axis O6) parallel to the vertical direction.

With the arm 104 having the above-described configuration, the six degrees of freedom are achieved for the movement of the imaging device 106 in the medical observation apparatus 100.

Note that the configuration of the arm 104 is not limited to the above example.

For example, FIG. 1 illustrates a configuration in which the arm 104 is provided with the counterweight 114, that is, a configuration in which the arm 104 is a balance arm. However, the arm 104 may have a configuration in which the counterweight 114 is not provided.

For example, each of the joints 110a, 110b, 110c, 110d, 110e, and 110f of the arm 104 may be provided with a brake that regulates rotation of each of the joints 110a, 110b, 110c, 110d, 110e, and 110f. Examples of the brake according to the present embodiment include brakes of any type, such as a mechanically driven brake and an electrically driven electromagnetic brake.

The driving of the brake (not illustrated) is controlled by, for example, a processor functioning as a control unit described later, or an external medical control apparatus (not illustrated). In the medical observation apparatus 100, an operation mode of the arm 104 is set with the driving of the brake controlled. The operation modes of the arm 104 include, for example, a full fixed mode, a partially fixed mode, and a free mode.

Here, the full fixed mode according to the present embodiment is, for example, an operation mode in which the position and posture of the imaging device 106 are fixed by restricting the rotation of each rotation axis provided on the arm 104 with the brake. When the arm 104 is in the full fixed mode, the operation state of the medical observation apparatus 100 is a fixed state in which the position and the posture of the imaging device 106 are fixed.

The partially fixed mode according to the present embodiment is, for example, an operation mode in which the position and posture of the imaging device 106 are partially fixed by restricting the rotation of some of the rotation axes provided on the arm 104 with the brake. For example, when the partially fixed mode is set, the rotation operation about the second axis O2 and the third axis O3 is enabled, and the rotation operation about the other axes is restricted. Needless to say, examples of the restriction when the partially fixed mode is set are not limited to the example described above.

In addition, the free mode according to the present embodiment is an operation mode in which the brake is released, so that rotation about each of the rotation axes provided on the arm 104 can be freely made. For example, in the free mode, the position and posture of the imaging device 106 can be adjusted by a direct operation by the operator. Here, the direct operation according to the present embodiment means, for example, an operation in which the operator holds the imaging device 106 with his or her hands and directly moves the imaging device 106.

[1-2-3] Imaging Device 106

The imaging device 106 is supported by the arm 104, and captures an image of an observation target such as a surgical site of a patient for example. The image capturing by the imaging device 106 is controlled by, for example, a processor functioning as the control unit described later, or an external medical control apparatus (not illustrated).

The imaging device 106 has a configuration corresponding to, for example, an electronic imaging type microscope.

Figure 3:
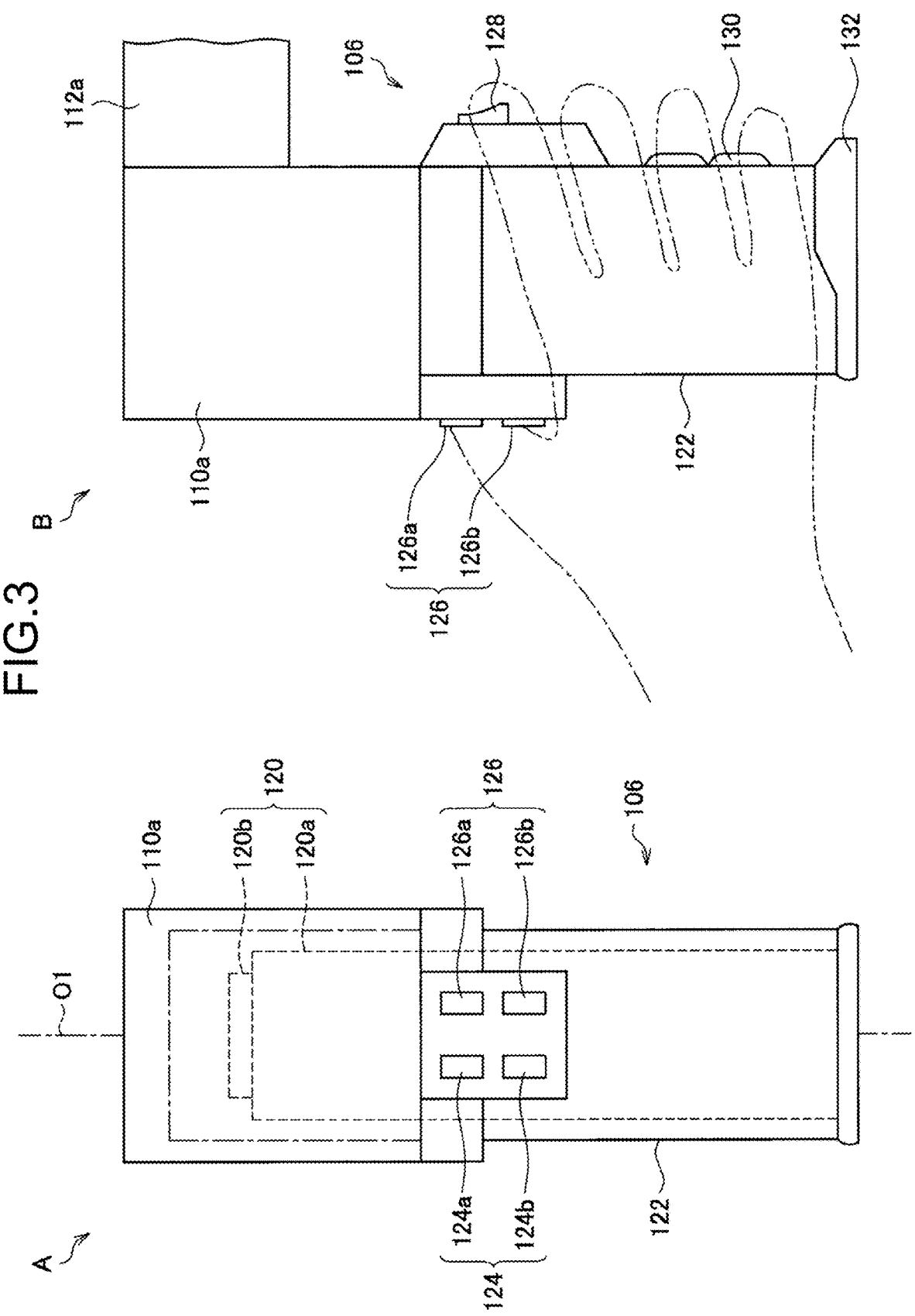
FIG. 3 is an explanatory diagram for describing an example of the configuration of an imaging device included in a medical observation apparatus according to the present embodiment.

FIG. 3 is an explanatory diagram for describing an example of the configuration of the imaging device 106 included in the medical observation apparatus 100 according to the present embodiment. FIG. 3 illustrates a case where the first axis O1 and the optical axis of the imaging device 106 are coaxial, and the optical axis of the imaging device 106 is directed vertically downward.

The imaging device 106 illustrated in FIG. 3 includes, for example, an imaging member 120 and a cylindrical member 122 having a substantially cylindrical shape. The imaging member 120 is provided inside the cylindrical member 122.

For example, a cover glass (not illustrated) for protecting the imaging member 120 is provided on an opening surface at a lower end (a lower side end in FIG. 3) of the cylindrical member 122.

Furthermore, for example, a light source (not illustrated) is provided inside the cylindrical member 122, and when an image is captured, the subject is irradiated with illumination light emitted through the cover glass from the light source. The reflected light (observation light) from the subject irradiated with the illumination light is incident on the imaging member 120 through the cover glass (not illustrated), whereby the imaging member 120 obtains an image signal (image signal indicative of a medical captured image) indicating the subject.

As the imaging member 120, it is possible to apply a configuration used in various known electronic imaging type microscope units.

For example, the imaging member 120 includes, for example, an optical system 120a and an image sensor 120b including an imaging element with which an image of an observation target is captured with light passing through the optical system 120a. The optical system 120a includes, for example, optical element such as one or more lenses such as an objective lens, a zoom lens, and a focus lens, and a mirror. Examples of the image sensor 120b include image sensors including a plurality of imaging elements such as a complementary metal oxide semiconductor (CMOS) and a charge coupled device (CCD).

The imaging member 120 includes two or more imaging devices including the optical system 120a and the image sensor 120b, to function as what is known as a stereo camera.

The imaging device of the imaging member 120 has one or more general functions of an electronic imaging type microscope unit, such as a zoom function (one of an optical zoom function and an electronic zoom function or both) and an auto focus (AF) function.

Furthermore, the imaging member 120 may have a configuration capable of capturing images with high a resolution such as 4K or 8K for example. When the imaging member 120 is configured to be capable of capturing a high resolution image, the image can be displayed on the display device 200 having a large display screen of, for example, 50 inches or more while guaranteeing a predetermined resolution (for example, Full HD image quality). Thus, the operator can see the display screen with improved visibility. Furthermore, when the imaging member 120 is configured to be capable of capturing a high resolution image, the captured image can be enlarged by the electronic zoom function and displayed on the display screen of the display device 200, while guaranteeing a predetermined resolution. Furthermore, when the predetermined resolution is guaranteed using the electronic zoom function, the performance of the optical zoom function in the imaging device 106 does not have to be so high. Thus, the optical system of the imaging device 106 can be simplified. As a result, the imaging device 106 can be made smaller.

The imaging device 106 is provided with various operation devices for controlling the operation of the imaging device 106, for example. For example, in FIG. 3, the imaging device 106 is provided with a zoom switch 124, a focus switch 126, and an operation mode setting switch 128. Needless to say, the installed positions and shapes of the zoom switch 124, the focus switch 126, and the operation mode setting switch 128 are not limited to the example illustrated in FIG. 3.

The zoom switch 124 and the focus switch 126 are examples of an operation device for adjusting an imaging condition in the imaging device 106.

The zoom switch 124 includes, for example, a zoom-in switch 124a for increasing the zoom magnification (magnification ratio) and a zoom-out switch 124b for decreasing the zoom magnification. When the operation on the zoom switch 124 is performed, the zoom magnification is adjusted, and the zoom is adjusted.

The focus switch 126 includes, for example, a distant view focus switch 126a for increasing the focal length to the observation target (subject) and a near view focus switch 126b for reducing the focal length to the observation target. By operating the focus switch 126, the focal length is adjusted, and the focus is adjusted.

The operation mode setting switch 128 is an example of an operation device for setting an operation mode of the arm 104 in the imaging device 106. When the operation on the operation mode setting switch 128 is performed, the operation mode of the arm 104 is changed. Examples of the operation mode changed by performing an operation on the operation mode setting switch 128 include the full fixed mode and the free mode. Thus, the operation mode setting switch 128 is an example of an operation device (first operation device) that can be operated to limit all degrees of freedom of the arm 104.

Examples of an operation on the operation mode setting switch 128 include an operation of pressing the operation mode setting switch 128. For example, while the operator is pressing the operation mode setting switch 128, the operation mode of the arm 104 is the free mode, and when the operator is not pressing the operation mode setting switch 128, the operation mode of the arm 104 is the full fixed mode.

The imaging device 106 is provided with, for example, a slipping prevention member 130 and a protrusion member 132 so that the operator can operate the various operation devices with higher operability and usability.

The slipping prevention member 130 is a member provided to prevent an operating body from slipping, for example, when the operator operates the cylindrical member 122 with the operating body such as his or her hand. The slipping prevention member 130 is formed of, for example, a material having a large coefficient of friction, and has a structure, such as recesses and protrusions, featuring a lower risk of slipping.

The protrusion member 132 is a member provided to prevent the operating body from blocking the visual field of the optical system 120a when the operator operates the cylindrical member 122 with the operating body such as his or her hand, and to prevent the cover glass (not illustrated) from being contaminated due to the operating body touching the cover glass when an operation is performed using the operating body.

Needless to say, the provided position and the shape of each of the slipping prevention member 130 and the protrusion member 132 are not limited to the example illustrated in FIG. 3. Furthermore, the imaging device 106 may not be provided with one of the slipping prevention member 130 and the protrusion member 132 or both.

An image signal (image data) generated by the imaging by the imaging device 106 is subjected to image processing in, for example, the processor functioning as the control unit described later. Examples of the image processing according to the present embodiment include one or more of various processing such as gamma correction, white balance adjustment, enlargement or reduction of an image related to the electronic zoom function, and pixel-to-pixel correction. When the medical observation system according to the present embodiment includes the medical control apparatus (not illustrated) for controlling various operations of the medical observation apparatus 100, the image processing according to the present embodiment may be executed by the medical control apparatus (not illustrated).

The medical observation apparatus 100 transmits, for example, a display control signal and an image signal as a result of the above-described image processing, to the display device 200.

With the display control signal and the image signal transmitted to the display device 200, the display screen of the display device 200 displays a medical captured image including the observation target (for example, a captured image including the surgical site). The image is displayed while being enlarged or reduced to a desired magnification by one of the optical zoom function and the electronic zoom function or both.

Note that the configuration of the imaging device 106 is not limited to the example illustrated in FIG. 3.

Figure 4:
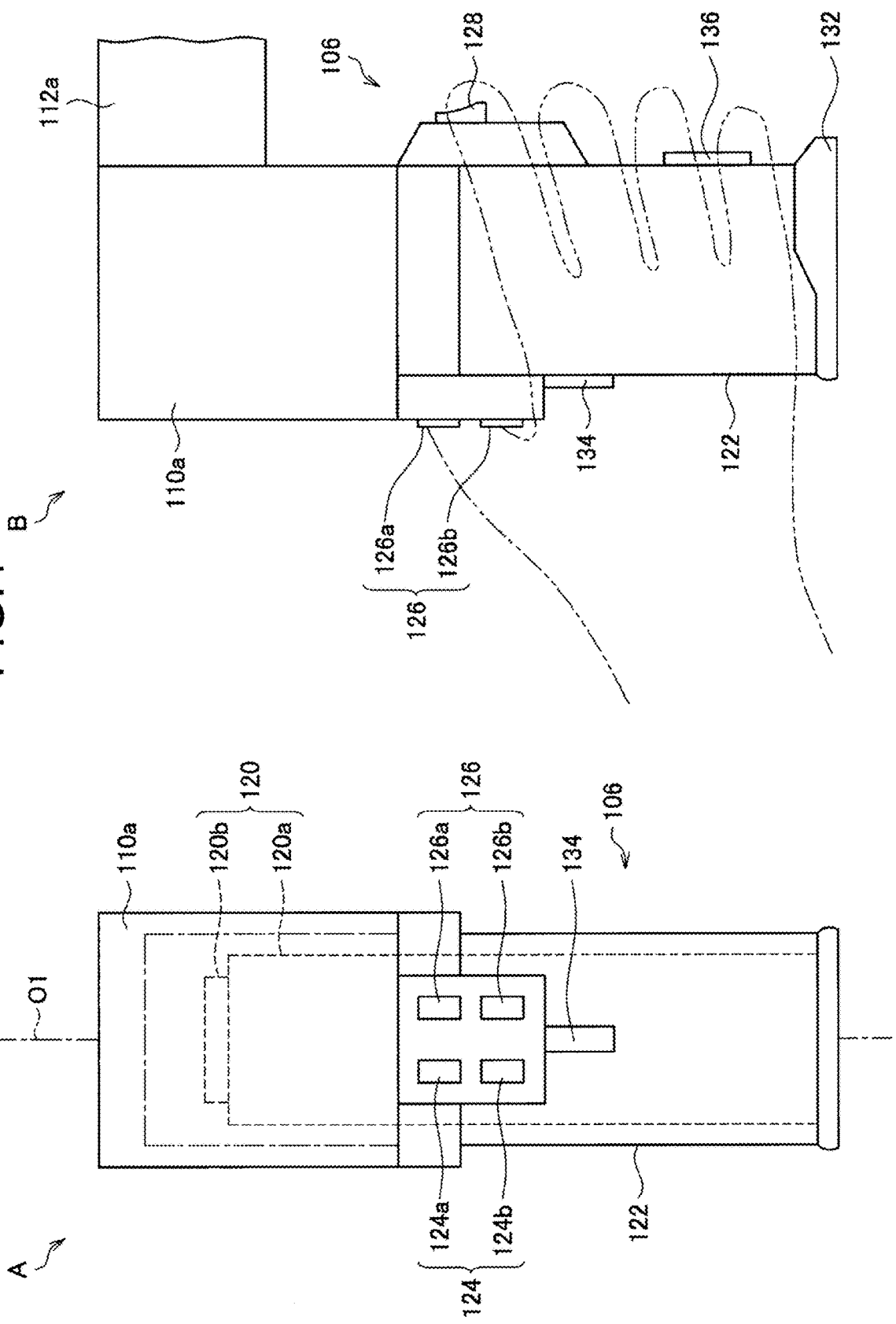
FIG. 4 is an explanatory diagram for describing another example of the configuration of the imaging device included in the medical observation apparatus according to the present embodiment.

FIG. 4 is an explanatory diagram illustrating an example of another configuration of the imaging device 106 of the medical observation apparatus 100 according to the present embodiment. FIG. 4 illustrates a case where the first axis O1 and the optical axis of the imaging device 106 are coaxial, and the optical axis of the imaging device 106 is directed vertically downward.

The imaging device 106 illustrated in FIG. 4 has basically the same configuration as the imaging device 106 illustrated in FIG. 3. The difference between the imaging device 106 illustrated in FIG. 4 and the imaging device 106 illustrated in FIG. 3 is that the imaging device 106 illustrated in FIG. 4 further includes operation mode setting switches 134 and 136.

The operation mode setting switches 134 and 136 are further examples of the operation device for setting the operation mode of the arm 104 in the imaging device 106. When the operation on the operation mode setting switches 134 and 136 is performed, the operation mode of the arm 104 is set to be the partially fixed mode. That is, the operation mode setting switches 134 and 136 are an example of an operation device (second operation device) that can be operated to restrict some of the degrees of freedom of the arm 104.

In the medical observation apparatus 100 including the imaging device 106 illustrated in FIG. 4, the operation mode of the arm 104 may be set to be the partially fixed mode by operating one of the operation mode setting switches 134 and 136.

Furthermore, although two switches (the operation mode setting switches 134 and 136) are illustrated as operation devices that can be operated to restrict some of the degrees of freedom of the arm 104 in FIG. 4, the operation device usable for performing the operation of restricting some of the degrees of freedom of the arm 104 may be one switch.

Examples of an operation on the operation mode setting switches 134 and 136 include an operation of pressing the operation mode setting switches 134 and 136. For example, while the operator is pressing the operation mode setting switches 134 and 136, the operation mode of the arm 104 is the partially fixed mode. As a specific example, while the operator is pressing the operation mode setting switches 134 and 136, the rotation operation about the second axis O2 and the third axis O3 is enabled, and the rotation operation about the other axes is restricted, for example.

When the operator is not pressing the operation mode setting switches 134 and 136, the operation mode of the arm 104 depends on the state of the operation on the operation mode setting switch 128. Furthermore, when both the operation mode setting switch 128 and the operation mode setting switches 134 and 136 are pressed, the operation mode of the arm 104 is the free mode. When both the operation mode setting switch 128 and the operation mode setting switches 134 and 136 are pressed, the operation mode of the arm 104 may be the partially fixed mode.

As illustrated in FIG. 4, the operation mode setting switch 128 (an example of the first operation device, the same applies in the following description) and the operation mode setting switches 134 and 136 (an example of the second operation device) are arranged on the upper and lower sides while the optical axis of the imaging device 106 is directed vertically downward. Specifically, when the optical axis of the imaging device 106 is directed vertically downward, the operation mode setting switches 134 and 136 are disposed more on the lower side than the operation mode setting switch 128.

When the operation mode setting switch 128 and the operation mode setting switches 134 and 136 are arranged as illustrated in FIG. 4, the following operations are implemented by an operation of the operator.

The operator holds the imaging device 106 so that both the operation mode setting switch 128 and the operation mode setting switches 134 and 136 are pressed. As a result, the operation mode of the arm 104 is the free mode, and the operator moves the imaging device 106 so that an image in a desired imaging range is captured. The operator releases the index finger to stop operating the operation mode setting switch 128. As a result, the operation mode of the arm 104 is partially fixed mode, and the movement of the arm 104 in a focusing direction is restricted. The operator finely adjusts the imaging range in the state where the movement of the arm 104 in the focusing direction is restricted, and releases his or her hand from the imaging device 106 when the fine adjustment is completed. As a result, the operation mode of the arm 104 is the full fixed mode, and thus the imaging range of the imaging device 106 is fixed.

In the above-described example, the target will not be out of focus under the partially fixed mode, and thus the operator does not need to firmly hold the imaging device 106. Thus, the operator can finely adjust the imaging range with his or her hand holding a medical instrument such as forceps. All things considered, the medical observation apparatus 100 including the imaging device 106 illustrated in FIG. 4 can improve the usability for the user such as the operator.

The medical observation apparatus 100 has, for example, the hardware configuration illustrated with reference to FIGS. 1, 3, and 4.

However, the hardware configuration of the medical observation apparatus according to the present embodiment is not limited to the configuration illustrated with reference to FIGS. 1, 3, and 4.

For example, the medical observation apparatus according to the present embodiment may not include the base 102, and may have a configuration in which the arm 104 is directly attached to the ceiling or the wall surface of the operating room or the like. For example, when the arm 104 is attached to the ceiling, the medical observation apparatus according to the present embodiment has a configuration in which the arm 104 is hung from the ceiling.

FIG. 1 illustrates an example in which the arm 104 is configured to implement six degrees of freedom for the driving of the imaging device 106. However, the configuration of the arm 104 is not limited to the configuration with the six degrees of freedom for the driving of the imaging device 106. For example, as described above, the arm 104 may have any degrees of freedom that is equal to or higher than three degrees of freedom including degrees of freedom implemented by a rotation operation about the first axis O1, the second axis O2, and the third axis O3. Thus, the number and arrangement of the joints and the links as well as the directions of the driving shaft of the joints can be set as appropriate so that the arm 104 can have the three degrees of freedom or higher.

FIGS. 1, 3, and 4 illustrate the example in which various operation devices for controlling the operation of the imaging device 106 are provided in the imaging device 106. However, some or all of the operation devices illustrated in FIGS. 1, 3, and 4 may not be provided in the imaging device 106. By way of example, the various operation devices for controlling the operation of the imaging device 106 may be provided in a section of the medical observation apparatus according to the present embodiment other than the imaging device 106. As another example, various operation devices for controlling the operation of the imaging device 106 may be any external operation device such as a foot switch or a hand switch including a remote controller.

Furthermore, the imaging device 106 may have a configuration enabling switching among a plurality of observation modes. Examples of the observation mode according to the present embodiment include an observation mode in which an image is captured using natural light, an observation mode in which an image is captured using special light, and an observation mode in which an image is captured using an image enhancement observation technique such as narrow band imaging (NBI). Examples of the special light according to the present embodiment include light in a specific wavelength band, such as light in a near-infrared wavelength band, or light in a fluorescence wavelength band for fluorescence observation using 5-Aminolevulinic Acid (5-ALA).

An example of the configuration of the imaging device 106 enabling switching among a plurality of observation modes includes "a configuration including: a filter that transmits light in a specific wavelength band and blocks light in the other wavelength bands; and a movement mechanism that selectively arranges the filter on an optical path". Examples of the specific wavelength band for transmission through the filter according to the present embodiment include: a near-infrared wavelength band (for example, a wavelength band from approximately 0.7 [micrometers] to 2.5 [micrometers]); a fluorescence wavelength band for fluorescence observation using 5-ALA (for example, a wavelength band from approximately 0.6 [micrometers] to 0.65 [micrometers]); and an indocyanine green (ICG) fluorescence wavelength band (for example, a wavelength band form approximately 0.82 [micrometers] to 0.85 [micrometers]).

Note that the imaging device 106 may be provided with a plurality of filters with different transmitted wavelength bands. Furthermore, in the above description, an example in which the filter is disposed on the optical path to capture an image with light in a specific wavelength band has been described. However, it is needless to say that the configuration of the imaging device 106 for capturing an image with light in a specific wavelength band is not limited to the example described above.

Figure 5:
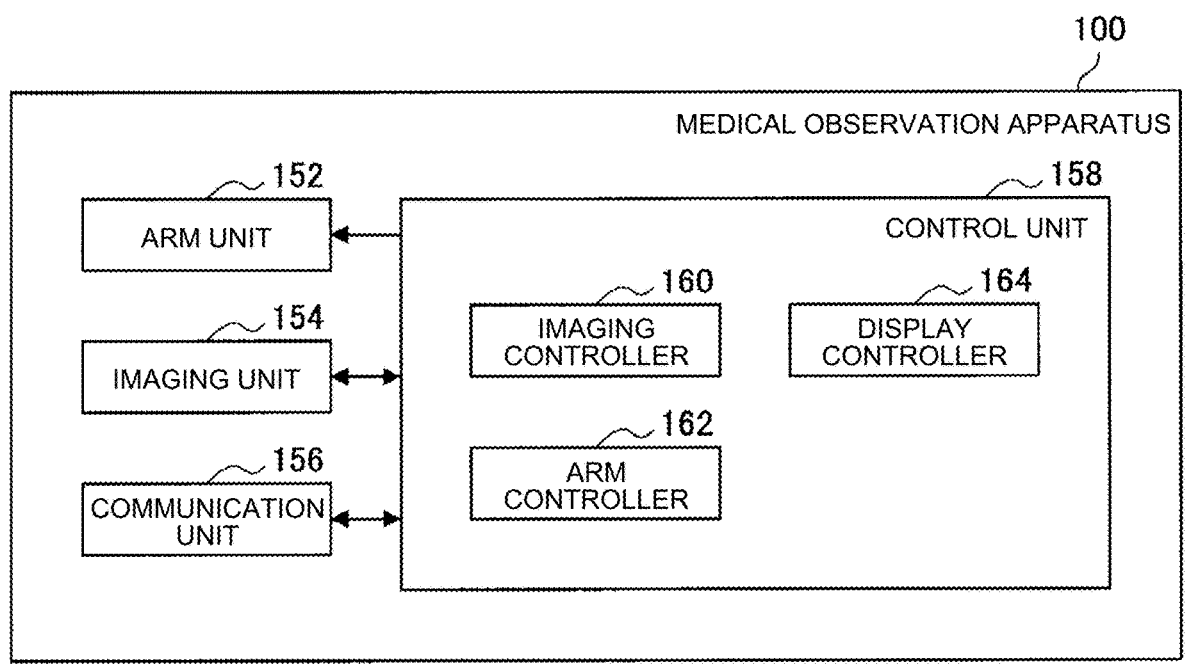
FIG. 5 is a functional block diagram illustrating an example of the configuration of the medical observation apparatus according to the present embodiment.

Next, the medical observation apparatus 100 illustrated in FIG. 1 will be described using functional blocks. FIG. 5 is a functional block diagram illustrating an example of the configuration of the medical observation apparatus 100 according to the present embodiment.

The medical observation apparatus 100 includes, for example, an arm unit 152, an imaging unit 154, a communication unit 156, and a control unit 158.

The arm unit 152 includes the arm 104 and supports the imaging device 106 forming the imaging unit 154.

The imaging unit 154 includes the imaging device 106, and captures an image of an observation target. The imaging by the imaging unit 154 is controlled by, for example, the control unit 158.

The communication unit 156 is a communication unit included in the medical observation apparatus 100, and is in charge of performing wireless or wired communications with an external device such as the display device 200. The communication unit 156 includes, for example, the above-described communication device (not illustrated). The communication by the communication unit 156 is controlled by, for example, the control unit 158.

The control unit 158 includes, for example, the above-described processor (not illustrated), and is in charge of controlling the entire medical observation apparatus 100. Furthermore, the control unit 158 is in charge of leading the processing in a control method described later. Note that the processing in the control method in the control unit 158 may be distributed among a plurality of processing circuits (for example, a plurality of processors) to be executed.

More specifically, the control unit 158 includes, for example, an imaging controller 160, an arm controller 162, and a display controller 164.

The imaging controller 160 controls the imaging device 106 forming the imaging unit 154. Examples of the control on the imaging device 106 include control on one or more general functions of an electronic imaging type microscope unit such as control on an AF function at least including a zoom function (the optical zoom function and the electronic zoom function).

The arm controller 162 controls the driving of the arm 104 forming the arm unit 152. Examples of the control on the driving of the arm 104 include "application of a control signal for controlling the driving to the actuator (not illustrated) corresponding to each of the joints 110a, 110b, 110c, 110d, 110e, and 110f".

Furthermore, the arm controller 162 is in charge of the processing in the control method described later. An example of the processing in the control method according to the present embodiment will be described later.

The display controller 164 transmits, for example, the display control signal and the image signal to a communication device (not illustrated) of the communication unit 156, and transmits the display control signal and the image signal to the display device 200, thereby controlling the displaying on the display device 200. Note that communication control in the communication unit 156 may be performed by a communication control unit (not illustrated) of the control unit 158. Furthermore, as described later, the display controller 164 can also be in charge of processing in the control method according to the present embodiment.

For example, the control unit 158 includes the arm controller 162 to be in charge of leading the processing in the control method according to the present embodiment. Furthermore, the control unit 158 includes the imaging controller 160, the arm controller 162, and the display controller 164 to be in charge of controlling the entire medical observation apparatus 100 for example.

Note that the functional configuration of the control unit 158 is not limited to the example illustrated in FIG. 4.

For example, the control unit 158 can have any configuration according to how the functions of the medical observation apparatus 100 are defined, such as a configuration according to how the processing in the control method according to the present embodiment is defined.

The medical observation apparatus 100 has the configuration illustrated in FIG. 5 to execute the processing in the control method according to the present embodiment, which will be described later for example.

Note that the functional configuration of the medical observation apparatus according to the present embodiment is not limited to the configuration illustrated in FIG. 5.

For example, the medical observation apparatus according to the present embodiment includes some or all of the imaging controller 160, the arm controller 162, and the display controller 164 illustrated in FIG. 5 separately from the control unit 158 (for example, with the units implemented in another processing circuit).

Furthermore, the functional configuration for implementing the processing in the control method according to the present embodiment in the medical observation apparatus according to the present embodiment is not limited to the configuration illustrated in FIG. 5. For example, the device can have a functional configuration according to how the processing in the control method according to the present embodiment is defined.

Furthermore, for example, when communications are performed with an external device via an external communication device having the same function and configuration as the communication unit 156, the medical observation apparatus according to the present embodiment may not include the communication unit 156.

Furthermore, when the medical observation system according to the present embodiment has a configuration including a medical control apparatus (not illustrated) and the medical observation apparatus according to the present embodiment is controlled by the medical control apparatus (not illustrated), the medical observation apparatus according to the present embodiment may not include the control unit 158.

The medical control apparatus (not illustrated), for example, includes a control unit that has the same functions and configuration as the control unit 158 to execute the processing in the control method according to the present embodiment described later, and control the operations of the components of the medical observation apparatus according to the present embodiment such as the arm unit 152 and the imaging unit 154. The medical control apparatus (not illustrated) communicates with the medical observation apparatus according to the present embodiment via a communication device provided therein or an external communication device connected thereto, to control the operations of the components of the medical observation apparatus according to the present embodiment.

Furthermore, when the medical observation system according to the present embodiment has a configuration including the medical control apparatus (not illustrated) and the medical observation apparatus according to the present embodiment is controlled by the medical control apparatus (not illustrated), the medical observation apparatus according to the present embodiment may have a configuration not including some of the functions of the control unit 158.

[2] Control Method According to the Present Embodiment

Next, the control method according to the present embodiment will be described. Hereinafter, a case will be described as an example where the processing in the control method according to the present embodiment is executed by the medical observation apparatus 100 (more specifically, for example, by the control unit 158 of the medical observation apparatus 100). As described above, in the medical observation system according to the present embodiment, the processing in the control method according to the present embodiment may be executed by the medical control apparatus (not illustrated).

[2-1] Overview of Control Method According to the Present Embodiment

When the operation mode of the arm 104 is the free mode, the user of the medical observation apparatus 100 can freely move the position of the imaging device 106. However, as described above, the degrees of freedoms of the arm 104 can be compromised depending on the posture of the arm 104 that supports the imaging device 106. When the degrees of freedom of the arm 104 are compromised, there may be "a case where the imaging device cannot be moved to capture an image in a desired imaging range, unless a user manually changes the posture of the arm". When such a case occurs, the usability for the user of the medical observation apparatus can be compromised.

Figure 6:
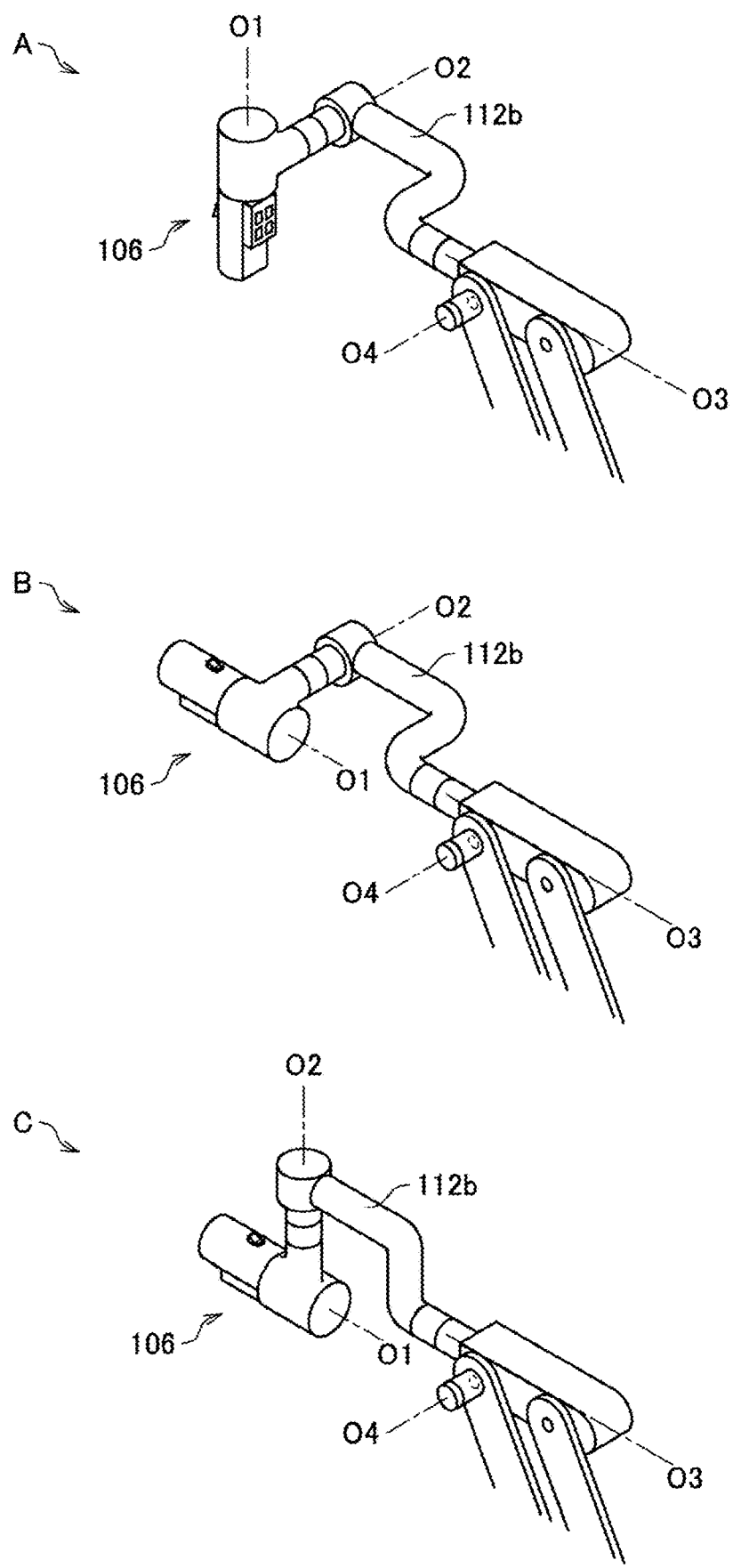
FIG. 6 is an explanatory diagram for describing an outline of a control method according to the present embodiment.

FIG. 6 is an explanatory diagram for describing an overview of the control method according to the present embodiment. A of FIG. 6 illustrates a first example of the posture of the arm 104. B of FIG. 6 illustrates a second example of the posture of the arm 104, and C of FIG. 6 illustrates a third example of the posture of the arm 104.

The posture according to the first example illustrated in A of FIG. 6 is achieved with the first axis O1, the second axis O2, and the third axis O3 being orthogonal to each other. In this state, the medical observation image is rotated by the rotation operation about the first axis O1. The imaging range of the imaging device 106 moves in the upward and downward direction (vertically, the same applies in the following description) by the rotation operation about the second axis O2, and moves in the left and right direction (a direction orthogonal to the vertical direction, the same applied in the following description) by the rotation operation about the third axis O3. The posture according to the first example illustrated in A of FIG. 6 does not result in the degrees of freedom being compromised or insufficient.

The posture according to the second example illustrated in B of FIG. 6 is achieved as a result of 90° rotation about the second axis O2 from the posture according to the first example illustrated in A of FIG. 6. Here, the medical observation image is rotated by the rotation operation about the first axis O1 and the rotation operation about the third axis O3. Furthermore, with the posture according to the second example illustrated in B of FIG. 6, when the imaging range of the imaging device 106 moves in the upward and downward direction through the rotation operation about the second axis O2, there is no movement component making the imaging range of the imaging device 106 move in the left and right direction. Thus, with the posture according to the second example illustrated in B of FIG. 6, the degrees of freedom are reduced from those with the posture according to the first example illustrated in A of FIG. 6, and are insufficient.

The posture according to the third example illustrated in C of FIG. 6 is achieved as a result of 90° rotation about the first axis O1 and the third axis O3 from the posture according to the second example illustrated in B of FIG. 6. Here, the medical observation image is rotated by the rotation operation about the first axis O1 and the rotation operation about the third axis O3, as in the case with the posture according to the second example illustrated in B of FIG. 6. Furthermore, with the posture according to the third example illustrated in C of FIG. 6, when the imaging range of the imaging device 106 moves in the left and right direction through the rotation operation about the second axis O2, there is no movement component making the imaging range of the imaging device 106 move in the upward and downward direction. Thus, with the posture according to the third example illustrated in C of FIG. 6, the degrees of freedom are reduced from those with the posture according to the first example illustrated in A of FIG. 6, and are insufficient.

For example, when the posture according to the second example illustrated in B of FIG. 6 or the posture according to the third example illustrated in C of FIG. 6 is established, rotation of the link 112b about the third axis O3 manually implemented by a user such as an operator involves the relative rotation about the second axis O2, whereby desired degrees of freedom of rotation can be achieved. However, when manually rotating the link 112b about the third axis O3, the user may need to perform an operation using both hands. As a result, the user may feel cumbersome.

Thus, the medical observation apparatus 100 controls the operations of the arm 104 to automatically guarantee the degrees of freedom in a case where the degrees of freedom are partially unavailable depending on the posture of the arm 104, as with the cases of the posture according to the second example illustrated in B of FIG. 6 and the posture according to the third example illustrated in C of FIG. 6. More specifically, the medical observation apparatus 100 controls the operations of the arm 104 to actively control the available degrees of freedom to automatically guarantee the degrees of freedom, when an input to move the arm 104 toward the side of the degree of freedom determined to have been unavailable.

The control on the operations of the arm 104 automatically guarantees the degrees of freedom determined to have been unavailable, whereby cumbersomeness felt by the user as described above is mediated. Thus, the medical observation apparatus 100 can improve the usability for a user using the medical observation apparatus 100.

[2-2] Processing in Control Method According to the Present Embodiment

Next, the processing in the control method according to the present embodiment will be described more in detail.

As described above, the medical observation apparatus 100 controls the operations of the arm 104 to actively control the available degrees of freedom, in response to the detection of an input to move the arm 104 toward the side of the degree of freedom determined to be have been unavailable.

The medical observation apparatus 100 can identify the posture of the arm 104 (or estimate the posture of the arm 104, the same applies in the following description) based on the rotation angle about each rotation axis of the medical observation apparatus 100 for example. Note that the method for identifying the posture of the arm 104 (or the method for estimating the posture of the arm 104) is not limited to the example described above, and the medical observation apparatus 100 may use any method with which the posture of the arm 104 can be identified, to identify the posture of the arm 104.

Here, "the input to make the arm 104 move toward the side of the degree of freedom determined to have been unavailable" means "an input to move the arm 104 with the posture in the predetermined state, about the rotation axis orthogonal to the second axis O2 and the third axis O3".

The posture of the arm 104 in the predetermined state according to the present embodiment, for example, is "a state where the first axis O1 is on a plane defined by the second axis O2 and the third axis O3" or "a state where the first axis O1 is on a plane parallel to the plane defined by the second axis O2 and the third axis O3", as with the cases of the posture according to the second example illustrated in B of FIG. 6 and the posture according to the third example illustrated in C of FIG. 6. The medical observation apparatus 100 determines whether the posture of the arm 104 is in the predetermined state by checking the relationship among the first axis O1, the second axis O2, and the third axis O3 in the posture of the arm 104 identified.

Note that the method of determining whether the posture of the arm 104 is in the predetermined state is not limited to the example described above. For example, the medical observation apparatus 100 may determine that the posture of the arm 104 is in the predetermined state when an input for moving the arm 104 about a rotation axis orthogonal to the second axis O2 and the third axis O3 is detected. With the predetermined state determined as described above, for example, when the operator tries to move the imaging device 106 in a difficult-to-move direction, the medical observation apparatus 100 can assist the movement of the imaging device 106 performed by the operator. Furthermore, with the movement of the imaging device 106 assisted by the medical observation apparatus 100, the operator can move the imaging device 106 using a smaller amount of force.

The inputs according to the present embodiment include, for example, one of "external force detected by a sensor for detecting an external force applied to the arm 104 such as a load cell" and "an operation signal corresponding to an operation on an external operation device such as a foot switch FS" or both. Hereinafter, the "input to move the arm 104 with the posture in the predetermined state about a rotation axis orthogonal to the second axis O2 and the third axis O3" may be referred to as "predetermined input".

In the example of the posture according to the second example illustrated in B of FIG. 6, the predetermined input may be "an input for moving the arm 104 to move the imaging range of the imaging device 106 in the left and right direction". In the example of the posture according to the third example illustrated in C of FIG. 6, the predetermined input may be "an input for moving the arm 104 to move the imaging range of the imaging device 106 in the upward and downward direction".

When a predetermined input is detected in the specified posture, the medical observation apparatus 100 rotates the link corresponding to the third axis O3 about the third axis O3. Here, the link corresponding to the third axis O3 according to the present embodiment is a link that is directly moved by the rotation operation about the third axis O3, and corresponds to the link 112b in the arm 104 with the configuration illustrated in FIG. 1.

Specifically, the medical observation apparatus 100 rotates the link 112b (an example of a link corresponding to the third axis O3, the same applied in the following description) clockwise, or rotates the link 112b counterclockwise.

Here, regardless of whether the link 112b is rotated clockwise or counterclockwise, an effect of automatically guaranteeing the degrees of freedom that have been unavailable due to the posture of the arm 104 is obtained. Therefore, the medical observation apparatus 100 may, for example, rotate the link 112b in a preset rotation direction, or may rotate the link 112b in a rotation direction determined according to a predetermined rule such as random. For example, when a distance sensor is provided to the arm 104, the medical observation apparatus 100 may rotate the link 112b in a rotation direction in which the rotation of the link 112b result in a longer distance from the object.

The medical observation apparatus 100 rotates the link 112b at a preset rotation speed, or rotates the link 112b at a rotation speed corresponding to a predetermined input magnitude. The medical observation apparatus 100 identifies, for example, the rotation speed corresponding to the predetermined input magnitude by using "a table (or database) in which magnitude of the external force and the rotation speed are associated with each other" (when the predetermined input is the external force detected by a sensor for detecting an external force applied to the arm 104) or "a table (database) in which an operation amount indicated by an operation signal and the rotation speed are associated with each other" (when the predetermined input is an operation signal corresponding to the operation on the external operation device).

The data indicating the preset rotation speed and each of the above tables are stored in, for example, a recording medium functioning as a storage unit (not illustrated). Note that the medical observation apparatus 100 may identify the rotation speed corresponding to the predetermined input magnitude by performing an operation of any algorithm with which the rotation speed can be obtained from the predetermined input magnitude.

Figure 7:
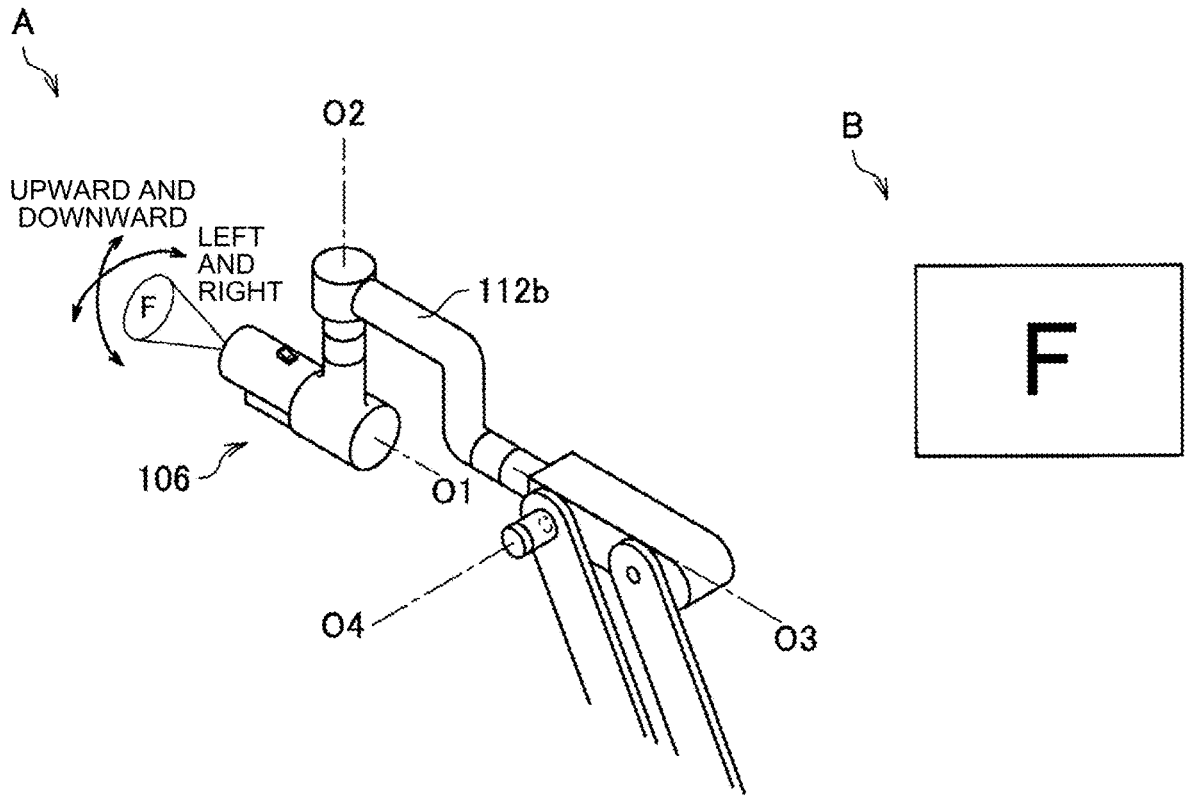
FIG. 7 is an explanatory diagram illustrating an example of processing in the control method according to the present embodiment.
Figure 8:
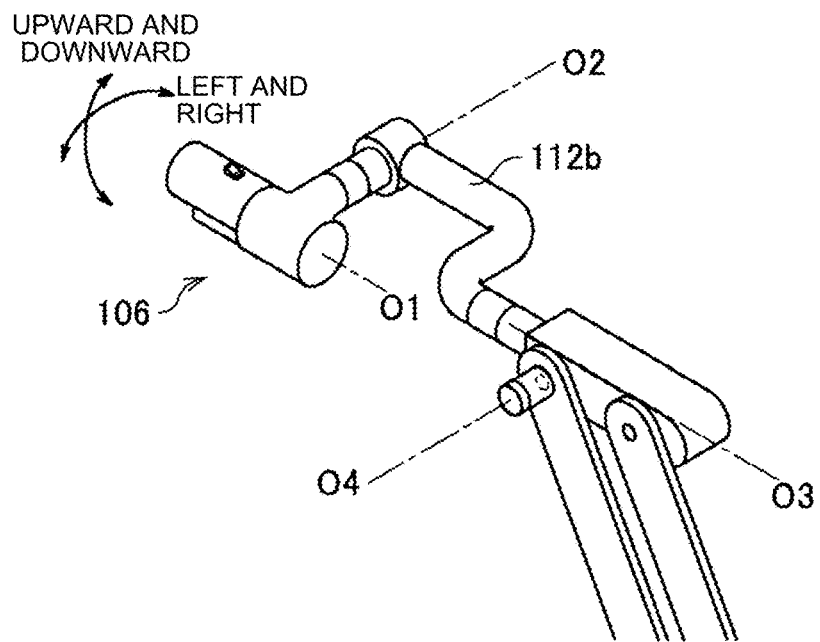
FIG. 8 is an explanatory diagram illustrating an example of the processing in the control method according to the present embodiment.

FIGS. 7 and 8 are explanatory diagrams illustrating an example of the processing in the control method according to the present embodiment. The posture of the arm 104 illustrated in A of FIG. 7 is the same as the posture according to the third example illustrated in C of FIG. 6. B of FIG. 7 illustrates an example of a medical captured image displayed on the display screen of the display device 200. The posture of the arm 104 illustrated in FIG. 8 is the same as the posture according to the second example illustrated in B of FIG. 6.

When the posture of the arm 104 illustrated in FIG. 7 is achieved in the movement of the position of the imaging device 106 by the operator, as described above with reference to C of FIG. 6, the imaging device 106 cannot be moved in the upward and downward direction due to the lack of a movement component for moving the imaging range of the imaging device 106 in the upward and downward direction.

In this case, the medical observation apparatus 100 identifies the "state where the first axis O1 is on the plane defined by the second axis O2 and the third axis O3" (an example where the posture of the arm 104 is in the predetermined state). Furthermore, for example, when an operator applies an external force to the arm 104 to move the imaging device 106 in the upward and downward direction, and the external force is detected by a load cell or the like, the medical observation apparatus 100 drives the actuator (not illustrated) for rotation about the third axis O3 to rotate the link 112*b*. Furthermore, for example, when an operator performs an operation of moving the imaging device 106 in the upward and downward direction on an external operation device such as the foot switch FS, and an operation signal corresponding to the operation is detected, the medical observation apparatus 100 drives the actuator (not illustrated) for rotation about the third axis O3 to rotate the link 112*b*. As a result, the arm 104 is in the posture illustrated in FIG. 8.

Here, when the arm 104 is in the posture illustrated in FIG. 8, as described with reference to B of FIG. 6, the imaging range of the imaging device 106 can be moved in the upward and downward direction by the rotation operation about the second axis O2. Thus, the medical observation apparatus 100 rotates the link 112*b* as described with reference to FIGS. 7 and 8, for example, so that the operator can move the imaging device 106 to the desired position without manually changing the posture of the arm 104.

Note that the processing in the control method according to the present embodiment is not limited to the example described above. The medical observation apparatus 100 may execute, as the processing in the control method according to the present embodiment, for example, one of processing according to a first example described in (1) below and processing according to a second example described in (2) below or both.

(1) First Example of Processing in Control Method

When the link 112*b* corresponding to the third axis O3 is rotated about the third axis O3, the rotation of the link 112*b* involves indirect rotation of the imaging device 106. As a result, the medical captured image captured by the imaging device 106 may also rotate.

Figure 9:
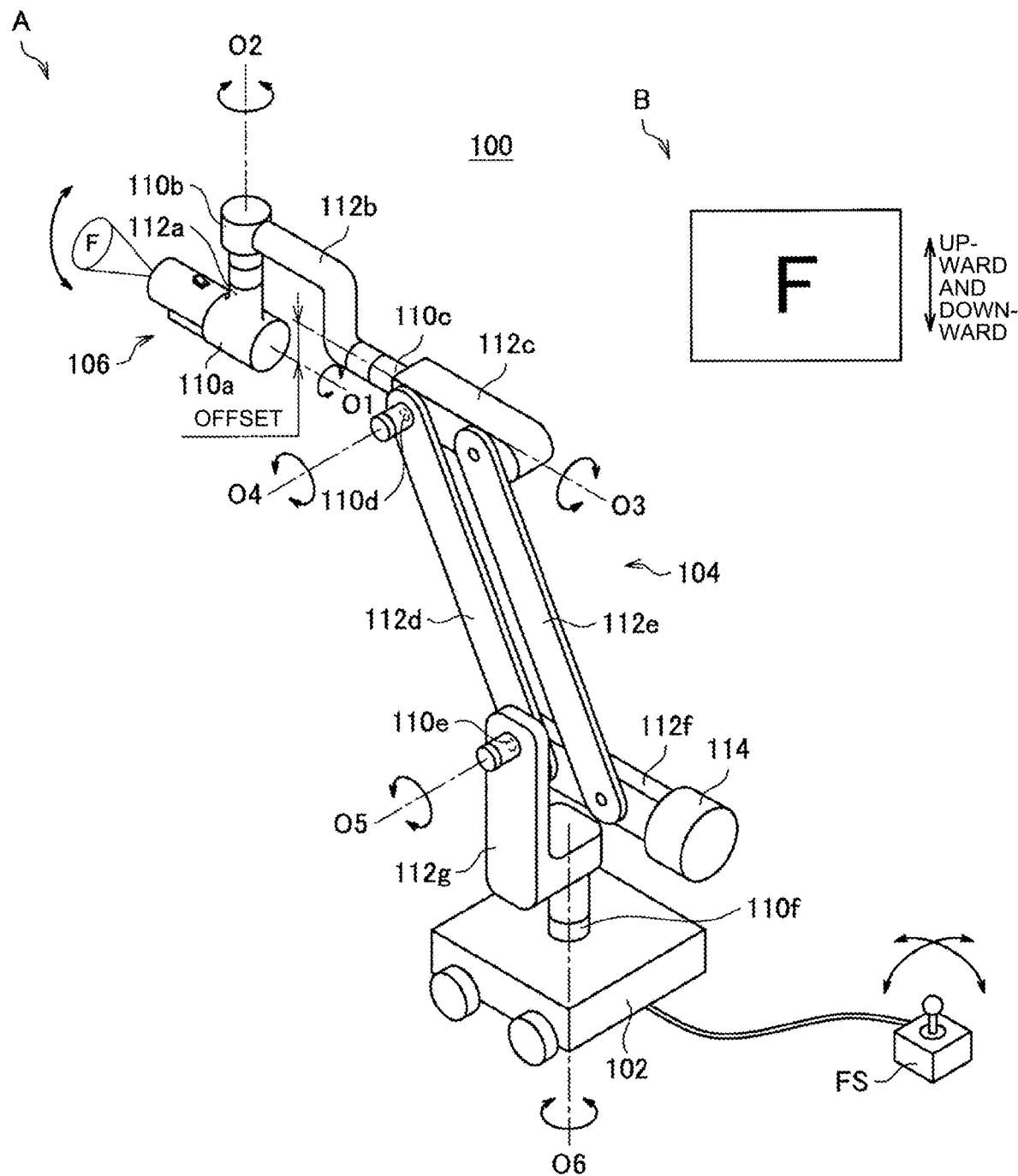
FIG. 9 is an explanatory diagram for describing an example of the processing in the control method according to the present embodiment.
Figure 10:
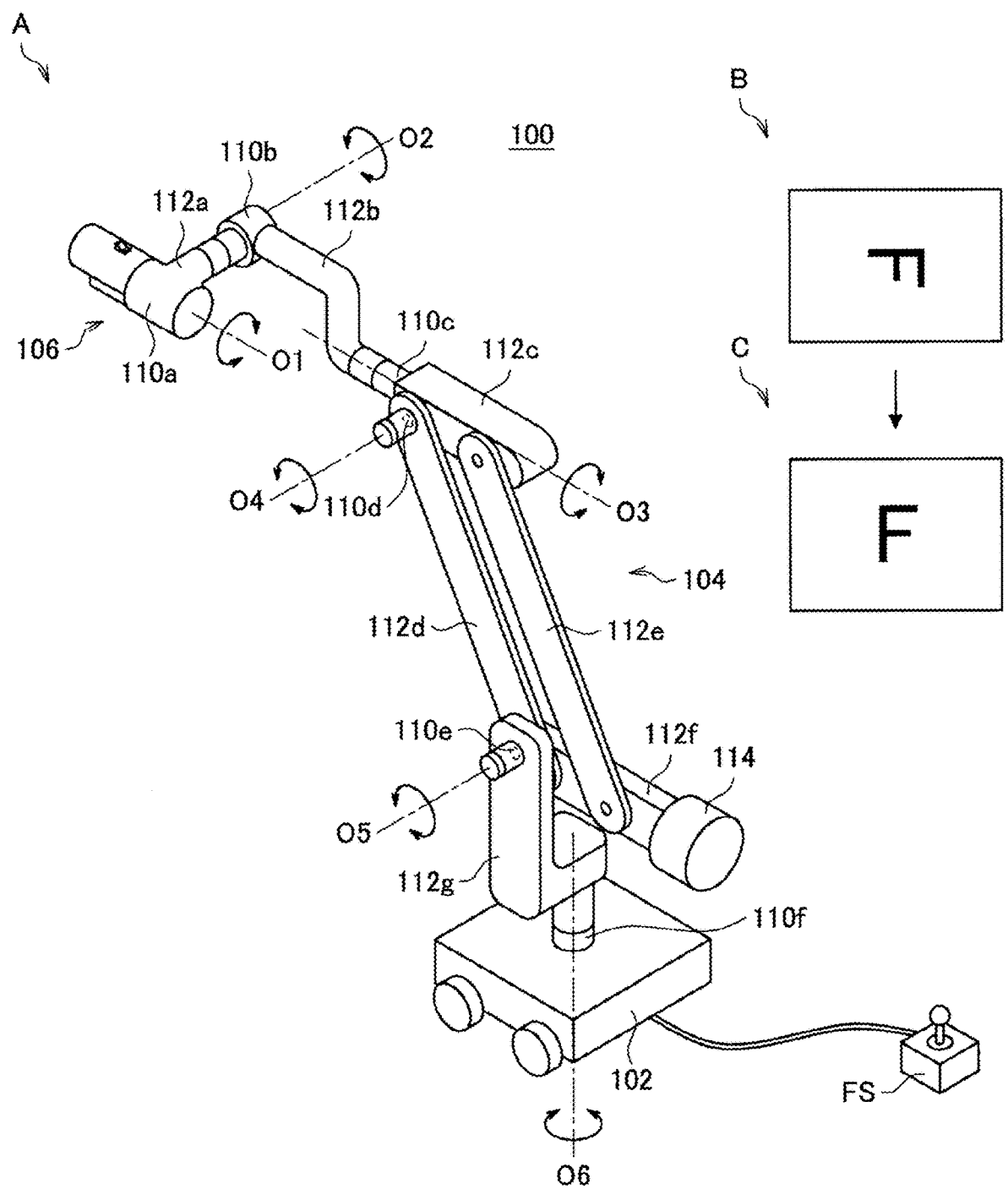
FIG. 10 is an explanatory diagram for describing an example of the processing in the control method according to the present embodiment.

FIGS. 9 and 10 are explanatory diagrams for describing an example of the processing in the control method according to the present embodiment. A of FIG. 9 and A of FIG. 10 illustrate the medical observation apparatus 100 having the same configuration as that in FIG. 1, together with the foot switch FS as an example of the external operation device. B of FIG. 9, B of FIG. 10, and C of FIG. 10 illustrate an example of a medical captured image displayed on the display screen of the display device 200.

When the posture of the arm 104 changes from the posture illustrated in A of FIG. 9 to the posture illustrated in A of FIG. 10 by rotating the link 112*b*, the imaging device 106 is also indirectly rotated by the rotation of the link 112*b*. B of FIG. 10 illustrates the result of this which is the medical captured image being displayed on the display screen as a rotated image of the medical captured image illustrated in B of FIG. 9.

Thus, when rotating the link 112*b* corresponding to the third axis O3 about the third axis O3, the medical observation apparatus 100 controls an operations of the arm 104, so that the orientation of the medical captured image after the rotation about the third axis O3 remains to be the same as the orientation of the medical captured image before the rotation about the third axis O3. More specifically, the medical observation apparatus 100 implements rotation about the first axis O1 to cancel out the rotation of the medical captured image due to the rotation about the third axis O3. An example of "an example in which the rotation about the first axis O1 is implemented so as to cancel out the rotation of the medical captured image due to the rotation about the third axis O3" includes "implementing the rotation about the first axis O1 by an amount that is the same as the amount of rotation about the third axis O3 in a direction opposite to the direction of the rotation about the third axis O3".

For example, as described above, by implementing the rotation about the first axis O1 to cancel out the rotation of the medical captured image due to the rotation about the third axis O3, the medical captured image is displayed on the display screen with the orientation remaining unchanged from that illustrated in B of FIG. 9, as illustrated in C of FIG. 10. Therefore, even when the link 112*b* is rotated, how the medical captured image is viewed does not change, whereby the operator is less likely to feel unnatural.

Note that "the method of making, when rotating the link 112*b* corresponding to the third axis O3 about the third axis O3, the orientation of the medical captured image after the rotation about the third axis O3 remain unchanged from the orientation of the medical captured image before the rotation about the third axis O3" is not limited to the example described above. For example, the medical observation apparatus 100 may execute image processing to cancel out the rotation of the medical captured image due to the rotation of the third axis O3. An example of the image processing includes "processing of rotating a medical captured image in a direction opposite to the direction of rotation about the third axis O3 by the same amount as the amount of rotation of the third axis O3". The image processing in the medical observation apparatus 100 is executed by the display controller 164, for example.

(2) Second Example of Processing in Control Method

For example, as in the offset illustrated in FIG. 9, when the first axis O1 and the third axis O3 are in a parallel state without being coaxial with each other, the center position of the imaging range (the center of the observation visual field) of the imaging device 106 moves in response to the rotation of the link 112b corresponding to the third axis O3 about the third axis O3. Thus, the rotation of the link 112b corresponding to the third axis O3 results in a positional shift of the visual field of the imaging device 106.

Thus, when rotating the link 112b corresponding to the third axis O3 about the third axis O3, the medical observation apparatus 100 controls an operation of the arm 104 to correct the positional shift of the visual field of the imaging device 106 due to the rotation of the link 112b corresponding to the third axis O3. For example, the medical observation apparatus 100 corrects the positional shift of the visual field of the imaging device 106 due to the offset illustrated in FIG. 9, by implementing rotation about some or all of the axes other than the first axis O1, the second axis O2, and the third axis O3, that is, the fourth axis O4, the fifth axis O5, and the sixth axis O6. As an example of the correction of the positional shift of the visual field of the imaging device 106, the medical observation apparatus 100 corrects the positional shift in the upward and downward direction by rotation about one of the fourth axis O4 and the fifth axis O5 or both.

Furthermore, the medical observation apparatus 100 corrects the positional shift in the left and right direction by rotating the sixth axis O6.

For example, with the positional shift of the visual field of the imaging device 106 corrected as described above, even when the link 112b is rotated, the center position of the imaging range of the imaging device 106 (the center of the observation visual field) remains unmoved. Thus, the operator is less likely to feel unnatural.

The method of preventing the positional shift of the visual field of the imaging device 106 in the case where the link 112b corresponding to the third axis O3 is rotated about the third axis O3 is not limited to the execution of the processing in the control method according to the second example.

For example, the medical observation apparatus 100 may have a configuration that can achieve a sufficiently small offset illustrated in FIG. 9, for example. Achieving sufficiently small offset illustrated in FIG. 9 includes eliminating the offset illustrated in FIG. 9 and achieving offset small enough to result in a positional shift of the visual field of the imaging device 106 that does not make the operator feel unnatural.

FIG. 11 is an explanatory diagram illustrating an example of the configuration of the medical observation apparatus 100 according to the present embodiment, and illustrates an example of a configuration achieving sufficiently small offset in FIG. 9. In FIG. 11, as in FIGS. 9 and 10, the foot switch FS is also illustrated as an example of the external operation device.

In the medical observation apparatus 100 having the configuration illustrated in FIG. 11, for example, the first axis O1 and the third axis O3 are coaxial to each other due to the shape of the link 112b, so that the offset illustrated in FIG. 9 is eliminated. Thus, in the medical observation apparatus 100 having the configuration illustrated in FIG. 11, even when the link 112b is rotated, the center position of the imaging range of the imaging device 106 (the center of the observation visual field) remains unmoved. Thus, the operator is less likely to feel unnatural.

[3] Example of Effects Achieved by Using Control Method According to the Present Embodiment The following effects can be achieved by using the control method according to the present embodiment for example. Needless to say, the effects achieved by using the control method according to the present embodiment are not limited to the examples described below.

- The medical observation apparatus 100 automatically guarantees the degrees of freedom by controlling the operations of the arm 104, whereby the operator can move the imaging device 106 to a desired position regardless of the posture of the arm 104.
- The medical observation apparatus 100 can assist movement of the imaging device 106 by the operator trying to move the imaging device 106 in a difficult-to-move direction. Thus, the operator trying to move the imaging device 106 in a difficult-to-move direction can move the imaging device 106 with a smaller amount of force.
- When the operator performs an operation using the foot switch FS, the operator can move the imaging device 106 to a desired position while holding a surgical tool in his/her hand, for example.

(Program According to the Present Embodiment)

The usability can be improved for the user of the medical observation apparatus with a program for causing a computer system to function as the medical observation apparatus according to the present embodiment (or the control apparatus according to the present embodiment) (for example, a program that can execute the processing in the control method according to the present embodiment) executed by a processor or the like in the computer system. The computer system according to the present embodiment includes a single computer or a plurality of computers. A series of processing in the control method according to the present embodiment is executed by the computer system according to the present embodiment.

Furthermore, effects provided by the displaying implemented by the processing in the control method according to the present embodiment can be obtained with the program for causing the computer system to function as the medical observation apparatus according to the present embodiment (or the control apparatus according to the present embodiment) executed by a processor or the like in the computer system.

As described above, the preferred embodiments of the present disclosure have been described in detail with reference to the accompanying drawings, but the technical scope of the present disclosure is not limited to such examples. It is apparent that a person having ordinary knowledge in the technical field of the present disclosure can arrive at various changes or modifications within the scope of the technical idea described in the claims. It is naturally understood that these also belongs to the technical scope of the present disclosure.

For example, in the above description, the program (computer program) for causing the computer system to function as the medical observation apparatus according to the present embodiment is provided, but the present embodiment can further provide a recording medium storing the program therein.

The configuration described above is an example of the present embodiment, and naturally belongs to the technical scope of the present disclosure.

Furthermore, the effects described in this specification are merely illustrative or exemplary, and thus are not limiting. Thus, the technique according to the present disclosure can exhibit other effects that are obvious to those skilled in the art from the description in the present specification, in addition to or instead of the above effects.

Note that the following configuration also belongs to the technical scope of the present disclosure.

(1)

A medical observation apparatus including:
an arm including a plurality of links connected to each other via a joint, the arm having at least three or more degrees of freedom implemented by a rotation operation about a rotation axis;
an imaging device supported by the arm; and
an arm controller configured to control an operation of the arm, wherein
when a posture of the arm is in a predetermined state, and when a predetermined input for moving the arm about a rotation axis orthogonal to a second axis that is a second rotation axis from a side of the arm on which the imaging device is supported and a third axis that is a third rotation axis from the side of the arm on which the imaging device is supported is detected, the arm controller rotates one of the links corresponding to the third axis about the third axis.

(2)

The medical observation apparatus according to (1), wherein
the predetermined state is
a state where a first axis that is a first rotation axis from the side of the arm on which the imaging device is supported is present on a plane defined by the second axis and the third axis, or
a state where the first axis is present on a plane in parallel with the plane defined by the second axis and the third axis.

(3)

The medical observation apparatus according to (1) or (2), wherein the predetermined input is an external force applied to the arm that is detected by a sensor configured to detect the external force.

(4)

The medical observation apparatus according to (3), wherein the sensor is disposed between a joint corresponding to the first axis that is the first rotation axis from the side of the arm on which the imaging device is supported and a joint corresponding to the second axis.

(5)

The medical observation apparatus according to any one of (1) to (4), wherein the predetermined input is an operation signal corresponding to an operation on an external operation device.

(6)

The medical observation apparatus according to any one of (1) to (5), wherein
when the link corresponding to the third axis is rotated about the third axis, the arm controller controls the operation of the arm so that an orientation of a medical captured image captured by the imaging device after rotation about the third axis remains unchanged from an orientation of the medical captured image captured by the imaging device before the rotation about the third axis.

(7)

The medical observation apparatus according to (6), wherein the arm controller implements rotation about the first axis that is the first rotation axis from the side of the arm on which the imaging device is supported, to cancel out rotation of the medical captured image due to the rotation about the third axis.

(8)

The medical observation apparatus according to any one of (1) to (7), wherein
when the link corresponding to the third axis is rotated about the third axis, the arm controller controls the operation of the arm to correct positional shift of a visual field of the imaging device due to rotation of the link corresponding to the third axis.

(9)

The medical observation apparatus according to any one of (1) to (8), wherein the arm controller rotates the link corresponding to the third axis clockwise or rotates the link corresponding to the third axis counterclockwise.

(10)

The medical observation apparatus according to any one of (1) to (9), wherein the first axis that is the first rotation axis from the side of the arm on which the imaging device is supported is coaxial with an optical axis of the imaging device.

(11)

The medical observation apparatus according to any one of (1) to (7), (9) and (10), wherein the arm is configured in such a manner that the first axis as the first rotation axis from the side of the arm on which the imaging device is supported and the third axis become coaxial by the rotation about the second axis.

(12)

The medical observation apparatus according to any one of (1) to (11), wherein
the imaging device includes:
a first operation device that is operable to restrict all of the degrees of freedom of the arm; and
a second operation device that is operable to restrict some of the degrees of freedom of the arm, and
the first operation device and the second operation device are arranged on upper and lower sides when the optical axis of the imaging device is directed vertically downward.

(13)

The medical observation apparatus according to (12), wherein the second operation device is disposed more on the lower side than the first operation device when the optical axis of the imaging device is directed vertically downward.

REFERENCE SIGNS LIST

100 medical observation apparatus
102 base
104 arm
106 imaging device
110a, 110b, 110c, 110d, 110e, 110f joint
112a, 112b, 112c, 112d, 112e, 112f, 112g link
120 imaging member
122 cylindrical member
124 zoom switch
126 focus switch
128, 134, 136 operation mode setting switch 152 arm unit
154 imaging unit
156 communication unit
158 control unit
160 imaging controller
162 arm controller
164 display controller
200 display device
1000 medical observation system

The invention claimed is:

1. A medical observation apparatus comprising:
an arm including a plurality of links connected to each other via a joint, the arm having at least three or more degrees of freedom;
an imaging device supported by the arm along a first axis that is a first rotation axis from a side of the arm on which the imaging device is supported; and
an arm controller configured to control an operation of the arm, wherein
when a posture of the arm is in a predetermined state, and when a predetermined input for moving the arm about a rotation axis orthogonal to a second axis that is a second rotation axis from the side of the arm on which the imaging device is supported and a third axis that is a third rotation axis from the side of the arm on which the imaging device is supported is detected, the arm controller rotates one of the links corresponding to the third axis about the third axis.

2. The medical observation apparatus according to claim 1, wherein
the predetermined state is
a state where the first axis is present on a plane defined by the second axis and the third axis, or
a state where the first axis is present on a plane in parallel with the plane defined by the second axis and the third axis.

3. The medical observation apparatus according to claim 1, wherein the predetermined input is an external force applied to the arm that is detected by a sensor configured to detect the external force.

4. The medical Observation apparatus according to claim 3, wherein the sensor is disposed between a joint corresponding to the first axis and a joint corresponding to the second axis.

5. The medical observation apparatus according to claim 1, wherein the predetermined input is an operation signal corresponding to an operation on an external operation device.

6. The medical observation apparatus according to claim 1, wherein
when the link corresponding to the third axis is rotated about the third axis, the arm controller controls the operation of the arm so that an orientation of a medical captured image captured by the imaging device after rotation about the third axis remains unchanged from an orientation of the medical captured image captured by the imaging device before the rotation about the third axis.

7. The medical observation apparatus according to claim 6, wherein the arm controller implements rotation about the first axis to cancel out rotation of the medical captured image due to the rotation about the third axis.

8. The medical observation apparatus according to claim 1, wherein
when the link corresponding to the third axis is rotated about the third axis, the arm controller controls the operation of the arm to correct positional shift of a visual field of the imaging device due to rotation of the link corresponding to the third axis.

9. The medical observation apparatus according to claim 1, wherein the arm controller rotates the link corresponding to the third axis clockwise or rotates the link corresponding to the third axis counterclockwise.

10. The medical observation apparatus according to claim 1, wherein the first axis that is the first rotation axis from the side of the arm on which the imaging device is supported is coaxial with an optical axis of the imaging device.

11. The medical observation apparatus according to claim 1, wherein the arm is configured in such a manner that the first axis and the third axis become coaxial by the rotation about the second axis.

12. The medical observation apparatus according to claim 1, wherein
the imaging device includes:
a first operation device that is operable to restrict all of the degrees of freedom of the arm; and
a second operation device that is operable to restrict some of the degrees of freedom of the arm, and
the first operation device and the second operation device are arranged on upper and lower sides when an optical axis of the imaging device is directed vertically downward.

13. The medical observation apparatus according to claim 12, wherein the second operation device is disposed more on the lower side than the first operation device when the optical axis of the imaging device is directed vertically downward.

* * * * *